United States Patent [19]

Högberg et al.

[11] 3,989,825

[45] Nov. 2, 1976

[54] SECONDARY PHOSPHORIC ACID ESTERS

[75] Inventors: Bertil Högberg; Hans Fex; Torsten Perklev; Sten Veige, all of Helsingborg; Bogoran Fredholm, Nyhamnslage, all of Sweden

[73] Assignee: Aktiebolaget Leo, Helsingborg, Sweden

[22] Filed: Aug. 14, 1972

[21] Appl. No.: 280,211

[30] Foreign Application Priority Data

Aug. 17, 1971 United Kingdom................ 38578/71
Jan. 31, 1972 United Kingdom................. 4510/72

[52] U.S. Cl................................ 424/212; 260/940; 260/941; 260/943; 260/944; 260/945; 260/930; 260/950; 260/951; 260/952; 260/953; 260/956; 260/964; 260/965; 424/206; 424/210; 424/211; 424/217; 424/218; 424/219; 424/225
[51] Int. Cl.$^2$...................... C07F 9/12; C07F 9/09
[58] Field of Search.................. 260/953, 951, 952; 424/212, 217

[56] References Cited
UNITED STATES PATENTS 3,297,631   1/1967   Bown et al...................... 260/953 X Primary Examiner—Anton H. Sutto
Attorney, Agent, or Firm—Gordon W. Hueschen

[57] ABSTRACT

This invention relates to novel secondary phosphoric acid esters and salts thereof, having valuable pharmacological properties, and to the preparation thereof. The invention is also concerned with pharmaceutical compositions containing the said compounds, and methods of treatment therewith.

The esters are i.a. useful as selective inhibitors of prostaglandins and of Slow Reacting Substances (SRS). They also inhibit the formation of adenosine 3',5'-monophosphate (cyclic AMP).

In addition the esters of this invention also exert intrinsic smooth muscle stimulatory activity.

21 Claims, No Drawings

SECONDARY PHOSPHORIC ACID ESTERS

The present invention relates to novel secondary phosphoric acid esters and salts thereof, having valuable pharmacological properties, as well as processes for the preparation thereof. The invention is also concerned with pharmaceutical compositions containing the said compounds, and methods of treatment therewith.

The compounds have all strong activity as selective inhibitors of prostaglandins or of compounds with structures related to the naturally occurring prostaglandins and having the same type of activities as these. They also selectively antagonize the Slow Reacting Substance (SRS), an unsaturated hydroxy-acid of lipid nature related to the prostaglandins and inhibit the formation of adenosine 3',5'-monophosphate (cyclic AMP), a key component of the cellular response to extracellular events, which is interrelated to the action of prostaglandin.

Like many substances with receptor blocking properties, e.g. certain adrenergic $\beta$-blocking agents, the compounds of this invention also exert intrinsic in this case smooth muscle stimulatory activity.

These esters are also useful as surface active agents and as agents in extractions of cations due to the presence of both hydrophilic and lipophilic groups in the same molecule. They also exert corrosion-inhibitory effects.

BACKGROUND OF THE INVENTION

The prostaglandins (in the following abbreviated as PG:s) are a new group of biologically active substances affecting many important physiological processes largely by influencing intracellular metabolism. See e.g. E. W. Horton in "Prostaglandins" (Monographs, Endocrinology, Vol. 7, 1972; Springer-Verlag).

The basic chemical structure of the PG:s is a $C_{20}$ fatty acid, prostanoic acid, containing a five-membered ring.

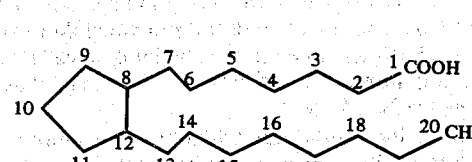

Depending on the substituents in the five-membered ring four different abbreviations are used in the literature.

All E-types PG:s have 11$\alpha$-hydroxy and 9-keto groups in the cyclopentane ring. In the F-types the 9-keto group is reduced to a ($\alpha$ or $\beta$) hydroxyl group. All the "primary" PG:s contain a 13:14 trans double bond. $E_1$ and $F_1$ compounds have only this one double bond the $E_2$ and $F_2$ molecules have an additional 5:6 cis double bond and the $E_3$ and $F_3$ a further cis double bond between 17 and 18. All naturally occurring PG:s found today have a 15(S)-hydroxy group. 9$\alpha$, 11$\alpha$, 15(S)-tri hydroxy-5-cis, 13-transprostadienoic acid has for example, been called prostaglandin $F_{2\alpha}$ and further abbreviated as $PGF_{2\alpha}$.

Details about the chemistry of the PG:s are found, e.g. in a review by P. W. Ramwell et al., in "Progress in the chemistry of fats and other lipids" vol. IX, p. 231.

It is also known that compounds with a structure related to the naturally occurring PG:s can have similar effects. See e.g. P. W. Ramwell et al., Nature 221 (1969) 1251, W. Lippman, J. Pharm. Pharmacol. 22 (1970) 65, J. Fried et al., J. Am. Chem. Soc. 97 (1971) 7319 and N. S. Crossley, Tetrahedron Letters (1971), 3327.

Evidence that PG:s are involved in a large number of physiological and pathological processes is rapidly accumulating. Two major areas, where these compounds play an important physiological role, are the control of fertility and the regulation of blood flow. Further, the PG:s have potent pharmacological actions on smooth muscle in various other organs such as the gastrointestinal and the respiratory tracts. They are also involved in the events following nerve stimulation, both centrally and in the periphery, as well as in the process of lipolysis. There are also indications that PG:s play an important role in different ophthalmologic disorders.

In the area of reproduction PG:s are involved in several ways. It is known, for instance, that sufficient amounts of PG:s to affect the female genital-tract smooth muscles are delivered with the semen and thereby probably promote conception. At full term the levels of PG:s in plasma and amniotic fluid are increased which in turn initiates the onset of labour. This latter effect of PG:s is presently being used therapeutically.

The circulatory effects of PG:s are as a rule vasodepressive, although PGF in some instances may cause a rise of the blood-pressure. The way in which PG:s normally contribute to blood-flow regulation has not yet been elucidated.

In the gastrointestinal tract PG:s generally cause contraction of the smooth muscle. Certain kinds of diarrhoea are believed to be caused by high plasma levels of PG:s. In the lungs PGF causes bronchoconstriction, while PGE has the opposite effect. At nerve

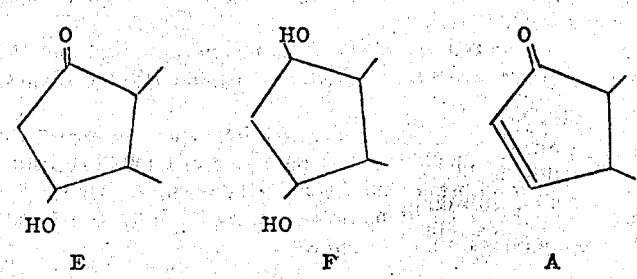

E     F     A     B stimulation PG:s are released and, at least in peripheral nerves, seem to counteract the result of the stimulation.

The effects of PG:s are generally obtained with very small amounts of the compounds, and this observation, together with the fact that PG:s are widely distributed in the organism point to an important role of these compounds in homeostatic mechanisms. However, although so many important pharmacological effects of PG:s are known, the exact nature of their physiological involvements is poorly understood. This is in part due to the fact that no suitable inhibitory compound has so far been available.

Having very pronounced physiological and pharmacological effects the PG:s could safely be anticipated also to play an important role in pathological conditions. Accordingly, there is now rapidly growing evidence for this, a fact that further emphasizes the need for prostaglandin-inhibitory agents. Thus, PG:s are involved in inflammatory processes of various kinds, such as burns, contact dermatitis and anaphylactic reactions. In these cases PG:s have been suggested to be mediators of the reaction. One important condition, for example, in which PG:s are considered to be of etiological significance, is bronchial asthma. In this connection it is of interest to mention that a substance, chemically and pharmacologically closely related to the prostaglandins, namely Slow Reacting Substance (SRS, Cf. Strandberg, K. and Uvnas, B. in Acta Physiol. Scand. 82 (1971) p. 358), is also produced during anaphylaxis, e.g. in bronchial asthma. A possibility to counteract the effect of this substance is thus also highly desirable.

Against the background of the above information it is evident that major therapeutic advances may result from the use of prostaglandin-inhibitory substances. Inhibition of various inflammatory reactions, improvement of bronchial asthma, regulation of bloodflow, control of gastrointestinal hypermotility are a few examples of expected therapeutic effects of such compounds. With increasing knowledge about the functions of PG:s the usefulness of inhibitors therefore will no doubt become still more apparent. Not only will conditions characterized by an excessive formation of PG:s be improved, but it is also possible to influence certain normal physiological processes when so desired, such as for example the conception.

Therapeutic advances may further result from administering esters of this invention before, at the same time or after the administration of PG:s in order to prevent side-effects caused by the PG:s, e.g. diarrhoea, nausea, vomiting, local tissue reactions and pyrexia.

The expression "prostaglandins" (PG:s) as used in this disclosure is intended to cover prostaglandins and related structures as indicated above of natural as well as synthetic origin.

In addition the esters of this invention exert an inhibitory action on the hormone stimulated formation of adenosine 3',5'-monophosphate (cyclic AMP). Cyclic AMP is formed from adenosine 5'-triphosphoric acid (ATP) by the action of adenyl cyclase, an enzyme system contained in the plasma membrane. The hormones influence this enzyme complex and thereby the intracellular concentration of cyclic AMP. The cells respond to the changes in cyclic AMP levels with whatever mechanism the different cells have available. It seems likely that compounds which influence the formation of cyclic AMP will be of therapeutic value, when increasing knowledge about the cellular dysfunction at different pathological conditions will be available. See e.g. G. A. Robinson et. al. in "Cyclic AMP," Academic Press, 1971.

Some antagonists of prostaglandins have already been described. J. Fried et. al., Nature 223 (1969) 208, found that 7-oxa-prostaglandin-like compounds with 6-membered rings inhibited prostaglandin $E_1$ ($PGE_1$).

A derivative of dibenzoxazepine was found to antagonize $PGE_2$ (J. H. Sanner in Arch. int. Pharmacodyn. 180 (1969) 46.)

A high molecular weight polyester between phloretin and phosphoric acid was also found to have a prostaglandin-blocking activity (K. E. Eakins et al. Brit. J. Pharmac. 39 (1970) 556), and in addition to be an antagonist of Slow Reacting Substance (SRS) (Mathe, A. A., and Strandberg, K. in Acta physiol. scand. 82 (1971) 460).

This polymer, polyphoretin phosphate, was already described by E. Diczfalusy et al. in Acta Chem. Scand. 7 (1953) 913, as a cross-linked high molecular weight enzyme inhibitor. It has an average molecular weight of 15000, did not dialyze through a cellophane membrane, and was found to be a strong inhibitor of various enzymes e.g. hyaluronidase and alkaline phosphatase.

These materials are complex mixtures of various different polymeric structures in varying proportions (due to the inability to control either the degree of polymerisation or selectively induce such polymerisation at specific reactions sites in view of the availability of numerous possible sites at which polymerisation can occur) and the activity which has been attributed thereto could not be attributed to any specific polymeric structure, much less any specific molecular weight fraction of any certain structures or units thereof, either in theory or in practice, in which latter aspect positive identification of specific active components of the complex polymeric mixture has been impossible.

It has now, surprisingly, been found that certain simple synthetic secondary phosphoric acid esters of the structures shown below are very good selective inhibitors of PG:s and compounds with prostaglandin activities and that they also selectively antagonize the Slow Reacting Substance (SRS). These effects are shown in examples Nos. 22–26.

From the results obtained in these examples it is obvious that the compounds of this invention are useful when it is desired to inhibit the effects caused by various PG:s and also of the effect of SRS.

Example No. 27 shows that the compounds also can prevent or reduce an anaphylactic bronchoconstriction.

The inhibitory effect of esters of this invention on the formation of cyclic AMP is described in example No. 28.

This example shows the usefulness of the compounds to prevent the formation of cyclic AMP and thus improve a condition where an excessive formation of that compound occurs.

In addition the esters of this invention exert a smooth muscle stimulatory activity as demonstrated in examples Nos. 29–31.

Since the compounds of the invention are produced synthetically, they have a definitive structure and are of course substantially free of inactive or lesser active impurities and materials of similar and/or indefinite composition and structure.

In the types of experiments described by Eakins et al. (ibid.) and by Perklev & Ahren (Life Sciences Part I, 10 (1971) 1387) most of the compounds of this invention are much stronger inhibitors against prostaglandins, e.g. E₁(PGE₁), E₂ (PGE₂), F₁α (PGF₁α) and F₂α (PGF₂α) than polyphloretin phosphate and they are also superior as antagonists for Slow Reacting Substance (SRS) in the types of experiments described by Mathe and Strandberg (ibid.). In addition the secondary phosphoric acid esters of this invention have no such antienzymatic properties as those described for this cross-linked high molecular weight polymer.

Some of the compounds according to the invention, for instance the bis(diethylstilbestrol)hydrogen phosphate, may possess a certain oestrogenic effect. Such compounds may primarily be used in the cases where such an additional effect is desirable or without importance.

SUMMARY OF THE INVENTION

Accordingly, one object of the invention is to provide new compounds possessing activity as selective inhibitors of prostaglandins and compounds with prostaglandin activities.

Another object of the invention is to provide new compounds possessing activity as selective inhibitors of the Slow Reacting Substances(SRS).

A further object of the invention is to provide new compounds possessing activity as inhibitors of the formation of adenosine 3', 5'-monophosphate (cyclic AMP).

Still another object of the invention is to provide new compounds having a smooth muscle stimulatory effect.

Another object of the invention is to provide processes for preparing the new compounds.

A further object of the invention is to provide a method of treating a living animal body to produce a prostaglandin inhibitory effect.

Yet another object of the invention is to provide a method of treating a living animal body to produce an antagonizing effect of the Slow Reacting Substance (SRS).

Still another object of the invention is to provide a method of treating a living animal body to produce an inhibition of the formation of adenosine 3', 5'-monophosphate (cyclic AMP).

Yet another object of the invention is to provide a method of treating a living animal body to produce a smooth muscle stimulatory effect.

A further object of the invention is to provide compositions containing as an active ingredient one or more of the new compounds preferably together with a pharmaceutically acceptable carrier and, if desired, other pharmacologically active agents.

According to the invention there are provided novel compounds having the general formula:

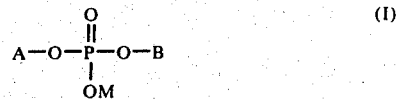
(I)

wherein
  M is selected from the group consisting of hydrogen and a pharmaceutically acceptable inorganic and organic cation, and
wherein
A and B, independent of each other, are:

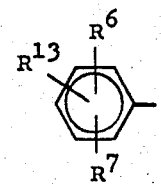

wherein
  one and only one of the substituents $R^6$, $R^7$, and $R^{13}$ always represents a group R, located in any of the ortho, meta and para positions relative to the phosphoric acid ester group, the group R having the formula:

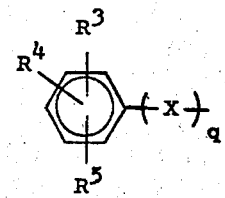

wherein
  $q$ is selected from the group consisting of zero and one; and wherein
  X is selected from the group consisting of:
    straight saturated hydrocarbon chains having at most 4 carbon atoms; and straight hydrocarbon chains having 2 to 4 carbon atoms and containing one double bond; wherein
  X above may be substituted by at most two substituents selected from the group consisting of;
    lower alkyl; lower alkenyl; lower alkoxy; hydroxy; —O—CO-$R^{14}$; cyclopentyl, cyclohexyl; phenyl; phenyl substituted in m- or p-position by one substituent selected from the group consisting of lower alkyl, lower alkoxy, —F, —Cl, —Br, and —CF₃; benzyl; benzyl substituted in m- or p-position by one substituent selected from the group consisting of lower alkyl, lower alkoxy, —F, —Cl, —Br, and —CF₃; benzylidene; benzylidene substituted in m- or p- position by one substituent selected from the group consisting of lower alkyl, lower alkoxy, —F, —Cl, —Br, and —CF₃; and lower alkylidene; with the proviso that not more than one substituent selected from the group consisting of: lower alkoxy; hydroxy; and —O—CO—$R^{14}$ is present in X; and that not more than one substituent selected from the group consisting of: cyclopentyl; cyclohexyl; phenyl; substituted phenyl; benzyl; substituted benzyl; benzylidene; and substituted benzylidene is present in X;
wherein
  B is the general formula (I) above also may be selected from the group consisting of:
    alkyl, having 1 to 8 carbon atoms, inclusive, optionally mono- and di-substituted; cycloalkyl, namely cyclopentyl and cyclohexyl, optionally mono- and di-substituted; 1- and 2- naphthyl, both optionally mono- and di-substituted; and

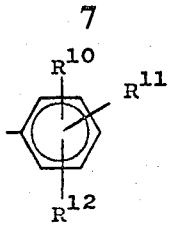

wherein
R³, R⁴, R⁵, R⁶, R⁷, R¹⁰, R¹¹, R¹² and R¹³ above are selected from the group consisting of:
hydrogen, lower alkyl; lower alkenyl; lower alkoxy; hydroxy; —O—CO—R¹⁴;

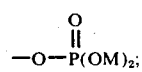

—F; —Cl; —Br; —CF₃; —CN; —CN; —NO₂; —COOR⁹; —CH₂COOR⁹; —OCH₂COOR⁹; —CO—R¹⁴; —CONR₂⁸; —CH₂CONR₂⁸; —OCH₂CONR₂⁸; —NR₂⁸; —NR⁸—CO—R¹⁴; —CH₂NR₂⁸; and —CH₂NR₂⁸-CO-R¹⁴;

with the proviso that always one and only one of the substituents R⁶, R⁷, and R¹³ is R; wherein
R⁸ is selected from the group consisting of hydrogen and lower alkyl; wherein
R⁹ is selected from the group consisting of lower alkyl and M, where M has the above meaning; and
wherein
R¹⁴ is lower alkyl;

In this disclosure the optional substitutions referred to above involve substituents selected from the group consisting of: lower alkyl; lower alkoxy; —F; —Cl; —Br, and —CF₃;

When B = A, resulting in symmetric secondary phosphoric acid esters, and q is zero, at least two of R³, R⁴, R⁵, R⁶, R⁷, and R¹³ are substituents other than hydrogen.

As used herein, the structural presentation of a substituted benzene nucleus as per the basic formula:

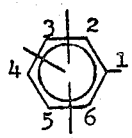

is intended to cover all possible variants with regard to the positions of the three nonfixed substituents, i.e., 2,3,4-, 2,3,5-, 2,3,6-, 2,4,5-, 2,4,6-, and 3,4,5-substitution.

In this disclosure the expression "lower" means that the group referred to contains one to four carbon atoms, inclusive. Thus, lower alkyl, lower alkenyl and lower alkoxy include for instance: methyl, ethyl, propyl, iso-propyl, butyl, secondary butyl, iso-butyl, tertiary butyl, vinyl, iso-propenyl, 1-propenyl, allyl, methoxy, ethoxy, propoxy, isopropoxy, butoxy, isobutoxy, secondary butoxy and tertiary butoxy.

Among pharmaceutically acceptable inorganic and organic cations under the definition of M above, those derived from the following metals and amines may be mentioned:
metals: calcium, potassium, and sodium,
amines: monoethanolamine, diethanolamine, dimethylaminoethanol, N-methylglucamine, trishydroxymethylmethylamine, morpholine, and the like.

Among the compounds covered by the above general formula (I) those are preferred wherein B is selected from the group consisting of: A as per the above definition; aryl, particularly phenyl; substituted aryl, particularly phenyl substituted as per the above definition; alkyl having at least four carbon atoms; and substituted alkyl having at least four carbon atoms.

With regard to substituents R¹⁰, R¹¹, and R¹², it is preferred that at least one of said substituents is hydrogen.

It is also preferred that, in addition to the one being R, at least one of substituents R³, R⁴, R⁵, R⁶, R⁷, R¹⁰, R¹¹, R¹², and R¹³ is different from hydrogen.

If substituents R³, R⁴, R⁵, R⁶, R⁷, R¹⁰, R¹¹, R¹², and R¹³ except the one being R, are all hydrogen, it is preferred that q is one and that X is a substituted straight hydrocarbon chain.

Concerning the substituent R, those compounds are preferred where R is positioned in one of the m- and p-positions relative to the secondary phosphoric acid ester group.

Preferred compounds are obtained if q is one and X is selected from the group consisting of unsubstituted and substituted straight hydrocarbon chains having at most three carbon atoms.

When q is one, preferred compounds are obtained if X is a straight hydrocarbon chain which carries at most two substituents, as per the above definition, selected from the group consisting of lower alkyl, lower alkenyl, lower alkoxy, hydroxy, —O—CO—R¹⁴, cyclopentyl, cyclohexyl, phenyl, substituted phenyl, benzyl, substituted benzyl, lower alkylidene, benzylidene, and substituted benzylidene.

If selected from the group consisting of —COOR⁹, —CH₂COOR⁹, —OCH₂COOR⁹, —CONR₂⁸, —CH₂CONR₂⁸, —OCH₂CONR₂⁸, —NR₂⁸, —NR⁸—CO—R¹⁴, —CH₂NR₂⁸, and —CH₂NR⁸—CO—R¹⁴, preferably only one of substituents R³, R⁴, R⁵, R⁶, R⁷, R¹³, and only one of substituents R¹⁰, R¹¹, and R¹² constitutes a substituent from said group.

A group of preferred compounds are those wherein the substituents R³, R⁴, R⁵, R⁶, R⁷, R¹⁰, R¹¹, R¹², and R¹³, except the one being R, are selected from the group consisting of hydrogen, lower alkyl, lower alkoxy, hydroxy, -O-CO-R¹⁴,

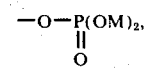

—F, —Cl, —Br, and —CF₃.

It is preferred that at most one of the substituents R³, R⁴, R⁵, R⁶, R⁷, R¹⁰, R¹¹, R¹², and R¹³ consists of the group

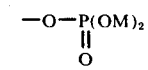

and that said group, which confers water solubility to the compounds hereby obtained, preferably is positioned in one of the groups R and B, when B is a substituted phenyl group, and located in any of the m- and p-positions relative to X or relative to the secondary phosphoric acid ester group, respectively.

If selected from the group consisting of —F, —Cl, —Br, and —CF₃, preferably at most two of substituents $R^3$, $R^4$, $R^5$, $R^6$, $R^7$, $R^{10}$, $R^{11}$, $R^{12}$, and $R^{13}$ constitute a substituent from said group.

Preferred compounds are also obtained when at least two of the substituents $R^3$, $R^4$, $R^5$, $R^6$, $R^7$, and $R^{13}$, except the one being R, are selected from the group consisting of lower alkyl, lower alkoxy, hydroxy, and —O—CO—$R^{14}$.

When B is a substituted phenyl group the substituents $R^{10}$, $R^{11}$, and $R^{12}$ are preferably selected from the group consisting of hydrogen, lower alkyl, lower alkoxy, —F, —Cl, and —$CF_3$.

Preparation of compounds having the formula (I) above.

The compounds having the above formula (I) may be prepared by methods known per se, see for instance Houben Weyl, Methoden der organischen Chemie, IV Ed. Vol. XII/2, p. 226. and the heading "Phosphorylation" by D. M. Brown, p. 75, in "Advances in Organic Chemistry" Vol. 3, Interscience Publishers, 1963.

Among such methods for instance the following are useful:

a. A compound having the formula A — OH i.e.

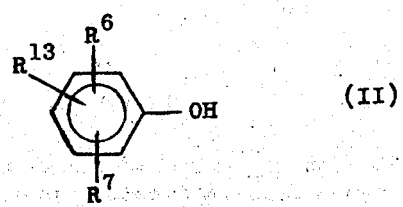

having only one free hydroxy group is allowed to react with about 0.5 mole of phosphorus oxychloride, suitably in the presence of a tertiary amine, for instance pyridine. After the esterification unreacted chlorine atoms are hydrolyzed with water and the symmetric secondary phosphoric acid ester obtained corresponding to the above formula (I) is isolated from the reaction mixture in the form of a free acid or as a suitable salt thereof.

If only 0.3 – 0.4 mole of phosphorus oxychloride is used a great number of corresponding tertiary phosphoric acid ester may also be formed. Such esters can be hydrolyzed, for instance with alkali, to give the desired symmetric secondary phosphoric acid esters corresponding to formula (I) above.

b. A compound having the formula (II) above and containing only one free hydroxy group is allowed to react with 0.5 mole of trichloroethyl phosphorodichloridate, $Cl_3CCH_2OP(O)Cl_2$, in the presence of at least 1 mole of a tertiary amine, e.g. pyridine. When both chlorine atoms of said chloridate have reacted the tertiary phosphoric acid obtained is treated with for instance Zn in pyridine-acetic acid or Zn/Cu in dimethylformamide to remove the trichloroethyl ether group resulting in a symmetric secondary phosphoric acid ester having the formula (I) above.

c. A compound of the formula II containing only one free hydroxy group is allowed to react with 0.5 mole of methylphosphoramidic dichloride in an inert organic solvent, for instance benzene, and in the presence of at least one mole of a tertiary amine, for instance triethylamine. The reaction may also be carried out using a suitable amine, for instance pyridine, as solvent. The bis-II N-methylphosphoramidate obtained is then hydrolyzed in an acidic solution, e.g. containing formic acid or sulfuric acid, giving a symmetrical secondary phosphoric acid ester having formula (I) above.

d. A primary phosphoric acid ester derived from a compound having the formula (II) thus having the general formula:

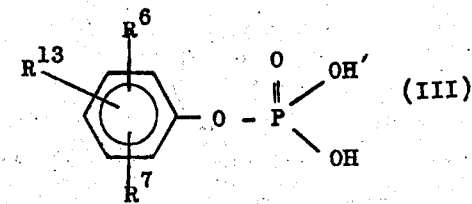

is allowed to react in an activated form with about one mole of a compound having formula B—OH. This reaction may for instance be carried out in the presence of about two moles of 2,4,6-triisopropylbenzenesulphonyl chloride and about two moles of a tertiary amine, e.g. triethylamine, using a suitable solvent, for instance pyridine. After the condensation has been completed water is added making it possible to isolate the secondary phosphoric acid having the formula (I) above.

With this type of reaction it is possible to prepare both symmetrical and unsymmetrical secondary phosphoric acid esters. Methods for the preparation of the primary phosphoric acid esters having the formula (III) are e.g. found in the first reference given above, p. 143, and in the second one.

e. The compounds having formula (I) above may also be prepared by the method described by J. Reiss in Bull. Soc. Chim. France 1965, p. 29 from a primary phosphoric acid ester of A-OH, i.e. having the formula (III) above, according to the reaction steps shown below:

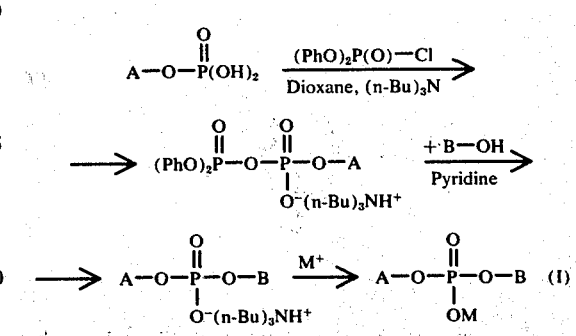

f. The compounds having formula (I) of the invention may also be prepared by using 2-chloromethyl-4-nitrophenyl phosphorodichloridate in the reaction steps shown below.

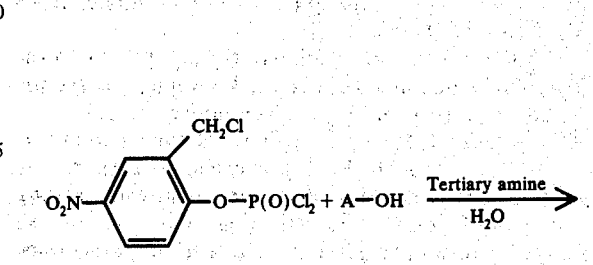

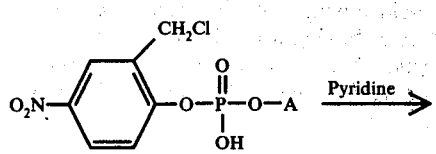

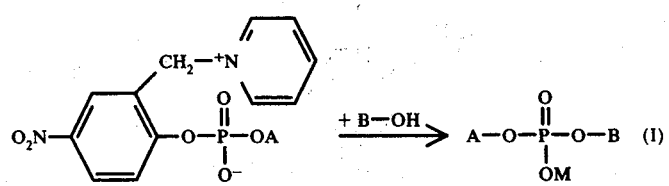

Using at least 2 moles of A-OH in the first step and in the presence of 2 moles of a tertiary amine, a tertiary phosphate ester is obtained in this step which then can be transferred over the quarternary pyridinium compound to a symmetrical secondary phosphoric acid ester having the formula (I) above.

g. The compounds having formula (I) above and wherein B is the same as A may also be prepared by hydrolyzing diphosphoric acid tetraesters, prepared in a manner known per se (see e.g. in the first regerence given above, p. 898), for instance according to the schematic reaction sequence indicated below

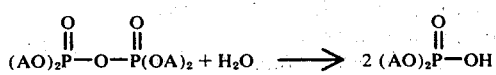

h. A compound of formula (II) above is treated with at least one mole of an aryl phosphorodichloridate having the formula

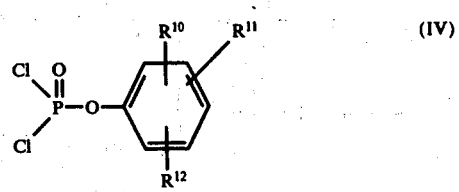

suitably in the presence of a tertiary amine, for instance dry pyridine. After the condensation unreacted chlorine atoms are hydrolyzed with water and the unsymmetrical secondary phosphoric acid ester obtained is isolated from the reaction mixture in the form of its free acid or as a suitable salt thereof.

Instead of the phosphorodichloridates having the formula (IV) above also phosphorodichloridates from naphthols can be used.

Methods for the preparation of the aryl phosphorodichloridates mentioned above are known per se, see for instance the first regerence given above (p. 212).

i. Compounds having formula (I) above wherein B is an alkyl or a cycloalkyl group may also be prepared by starting with a primary phosphoric acid ester having formula (III) above, and activating such esters for instance by means of a carbodiimide or trichloro-acetonitrile and under such activated conditions reacting them with an aliphatic or cycloaliphatic alcohol to give the corresponding unsymmetrical secondary phosphoric acid esters.

j. The compounds according to the present invention wherein B is an alkyl or cycloalkyl group may also be prepared by subjecting diphosphoric acid (pyrophosphate) triesters, having the formula (V) below, to a solvolysis with the appropriate alcohol, for instance according to the reaction sequence:

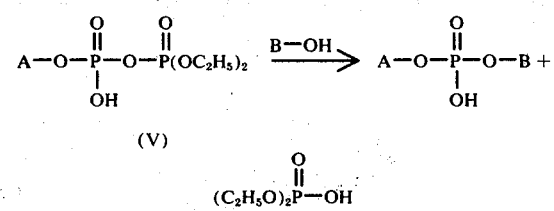

The diphosphoric acid triesters of formula (V) are prepared according to methods known per se, see for instance the first reference given above (p. 895).

k. The compounds having formula (I) above may also be prepared by converting, in a manner known per se, derivatives thereof, for instance tertiary esters with a lower aliphatic alcohol, a phosphoric acid diester amide or a phosphoric acid diester halogenide, to secondary phosphoric acid esters of formula (I). This may be illustrated by the following reaction formulas, wherein A and B have the above meaning.

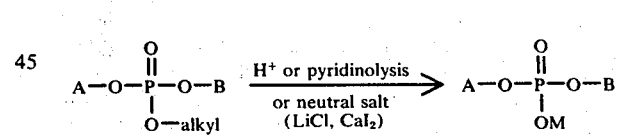

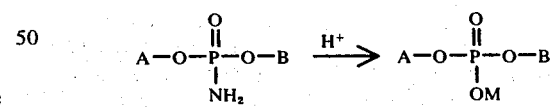

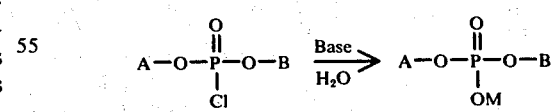

l. The compounds having the formula (I) may also be prepared according to Houben-Hoesch reaction (Friedel-Craft and Related Reactions III, 383, Interscience, New York, 1964) by reacting a compound

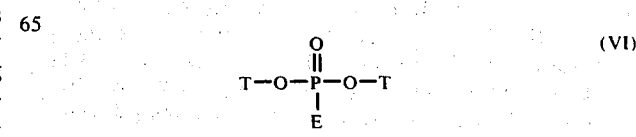

wherein T is

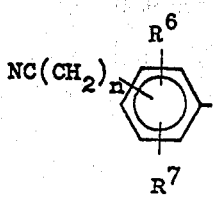

wherein $R^6$ and $R^7$ are different from R and n=0–3; and wherein E is or by conventional methods can be transformed to -OM; with a compound

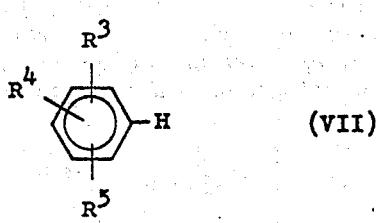

in which at least two of the substituents $R^3$, $R^4$ and $R^5$ are selected from —OH and —$OCH_3$ and located in m-position to each other, under formation of intermediate compounds

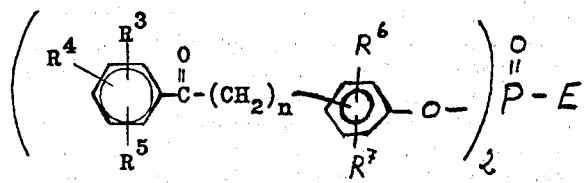

wherein $R^3$, $R^4$ and $R^5$ are the same as in the compound (VII) used and $n = 0$-3. These intermediates are then converted by reduction of the keto groups, and, if required, conversion of E to OM to compounds (I) wherein R is

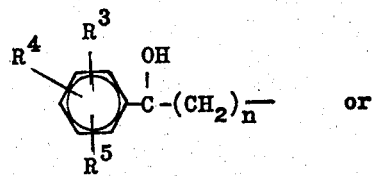

or

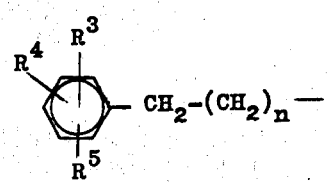

wherein $R^3$, $R^4$ and $R^5$ are the same as in (VII) and $n =$ 0-3.

m. The compounds having the formula (I) may also be prepared according to the schematic reaction indicated below.

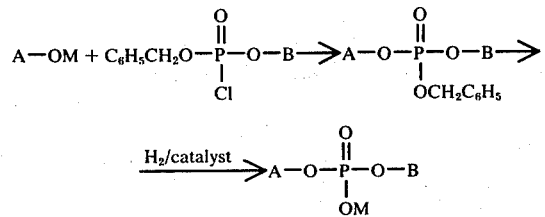

or OH or neutral salt n. It is also possible to prepare the compounds having formula (I) according to the present invention by first preparing a secondary phosphoric acid ester, wherein one or several of the substituents $R^3$, $R^4$, $R^5$, $R^6$, $R^7$, $R^8$, $R^9$, $R^{10}$, $R^{11}$, $R^{12}$, $R^{13}$, $R^{14}$ consists of other groups than those desired, and then converting such groups in a manner known per se into the groups defined by the general formula (I).

As examples of such transformations, besides that mentioned in 1 above, the removing of protecting groups, e.g. benzyl-, trityl-, methoxymethyl-, tetrahydropyranyl-, trimethylsilyl-, carboalkoxy-, carbobenzoxy-, and benzoyl groups, may be mentioned.

o. It is also possible in a manner known per se to prepare compounds having the general formula (I) from other compounds within the definition of the general formula (I).

As examples of such transformations the following methods may be mentioned: Free hydroxyl groups are e.g. obtained by removal of acyl- and dihydroxy-phosphinyl groups from acyl esters and primary phosphoric acid esters, respectively, by removal of lower alkyl groups from lower alkoxy groups, and via diazonium salts from primary aromatic amines. Free amino groups are e.g. obtained by removal of acyl groups in acylamides, by reduction of nitro-, nitrile- and amide groups. Free carboxlic acid groups are e.g. obtained by hydrolysis of ester-, amide- and nitrile groups. On the other hand free hydroxy groups can be esterified and etherified, primary and secondary amines acylated to amides, and carboxylic acids esterified and also transformed to amides. By Mannich reaction it is possible to insert aminomethyl groups, and by Schiemann and Sandmayer reactions primary aromatic amines can be converted to fluor-, chloride- or nitrile groups.

As far as the group X is concerned examples of tranformations which can be done within this group are found below when the methods to prepare A—OH, i.e. (II) are exemplified.

p. If the secondary phosphoric acid esters having the above formula (I) are isolated in the form of the free acids, such acids can be transferred to salts with pharmaceutically acceptable inorganic or organic cations in a conventional way. Examples of suitable inorganic and organic cations are found above.

When a secondary phosphoric acid ester according to this invention is isolated in the form of a salt with a cation, which is not pharmaceutically acceptable, such salt is transferred to the free acid or to salts with pharmaceutically acceptable cations according to methods known per se, for instance by treatment of a salt with a strong acid, by using a suitable ion exchanger or by carrying out a double decomposition in a suitable solvent.

The methods used when synthesizing the secondary phosphoric acid esters of the invention have to be chosen in such a way that all groups in the starting materials involved are compatible with the method used or, if necessary, sensitive groups are protected during the reaction and then converted to the desired groups so that compounds of the general formula (I) above are obtained.

The hydroxy compounds A-OH, i.e. (II), or functional derivatives thereof, used as starting materials in the preparation of the secondary phosphoric acid esters of the general formulas (II) and (III), are prepared according to known methods. Among useful methods to prepare those compounds which have two benzene rings connected with the group X or a group $R^{25}$, different from X, which can be converted to the group X by known methods at any suitable stage during the preparation of the secondary phosphate esters, the following types of reactions may be mentioned: Acetoacetic ester synthesis, Baeyer reaction, Benzoin condensation, Blaise ketone synthesis, Buchner-Curtius-Schlotterbeck reaction, Claisen-Schmidt condensation, Friedel-Crafts reaction, Fries rearrangement, Grignard reaction, Houben-Hoesch reaction, Knoevenagel condensation, Malonic ester synthesis, Necki reaction, Ullman reaction and Wittig reaction.

In all these types of reactions, appropriated substituted benzene compounds are used to form the compound A—OH, a functional derivative thereof, or a compound having two appropriated substituted benzene rings connected to each other by a group $R^{25}$, which by conventional methods in one or more reaction steps, can be converted to the desired compound A—OH or a functional derivative thereof.

As examples of transformations in the group X (or $R^{25}$) the following reactions can be mentioned.

If X (or $R^{25}$) carries a carbonyl group such group can be converted to a hydroxyl group, for instance by catalytic reduction, by Meerwein-Ponndorf-Verley reduction or by reduction with metal hydrides, e.g. $LiAlH_4$; or to a methylene group, e.g. by catalytic reduction, by Clemmensen reduction, by Wolff-Kishner reduction or by reduction with metal hydrides in the presence of $AlCl_3$.

Double bonds in X (or $R^{25}$) can be formed by elimination reactions. They can be hydrogenated catalytically, also in the presence of a carbonyl group, or new substituents can be inserted by addition reactions.

To insert groups like lower alkyl, lower alkylidene, phenyl, benzyl and benzylidene in X (or $R^{25}$) methods are found in references given below or in the examples of preparation.

Further details about the name reactions mentioned above are found e.g. in The Merck Index, 8th Ed., 1968, in the topic "Organic name reactions", p. 1137, and in references given there. Other references to these and other useful methods are found in reviews such as: Chem. Revs. 57 (1957) 281; Ind. Chim. Belg. (1961) 345; Organic Reactions 18 (1970) 1; and in monographs such as: T. A. Geismann, "The Chemistry of Flavonoid Compounds" (New York, 1962), p. 286; G. A. Olah, "Friedel-Crafts and Related Reactions", vol. II, part 1, and vol. III, part I (New York, 1964); and C. A. Buchler, D. E. Pearson, "Survey of Organic Syntheses" (New York, 1970), p. 623.

The reactions mentioned above to prepare A—OH (II). or functional derivatives thereof, are carried out in such a manner that each group of the compounds involved is compatible with the process in question or protected when necessary.

When the compounds A—OH (II) also carry other reactive groups such as —OH, primary and secondary amines and carboxylic acids, these groups are, when necessary, protected during the synthesis of the phosphate esters. Suitable protecting groups for —OH and amines are found in the monographs, S. Patai, "The Chemistry of the Hydroxyl Group" (London, 1971), p. 1001, and S. Patai, "The Chemistry of the Amino Group" (London, 1968), p. 669. A free carboxylic acid group can, for instance, be protected by converting it to a suitable ester. Such protecting group or groups can then be removed by any suitable stage during the preparation of the secondary phosphoric acid esters.

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in anyone of various ways, for example orally as in capsules or tablets, parenterally in the form of sterile solutions, suspensions and by pellet implantation. Among routes of parenteral administration are intravenously, subcutaneously, intramuscularly, intraperitoneally, intraarticularly, intradermally and subconjunctivally. Other modes of administration are lingually, vaginally, rectally, by aerosol and topically as e.g. in the form of ointments, eye-drops etc.

As representative of living animal bodies, which may be treated with the compounds and compositions of the invention, and according to the method of treatment of the invention, for alleviation of the same and/or similar conditions as those described, the following may be mentioned: domestic animals such as dogs and cats, farm animals such as horses, cows, sheep and goats.

Pharmaceutical formulations are usually prepared from a predetermined quantity of one or more of the compounds of the invention. Such formulations may take the form of powders, syrups, suppositories, ointments, eye-drops, elixirs, solutions, aerosols, pills, capsules, pellets or tablets, suspensions, emulsions, oil solutions etc., with or without, but preferably with, any one of a large variety of pharmaceutically acceptable vehicles or carriers. When in admixture with a pharmaceutical vehicle or carrier, the active ingredient usually comprises from about 0.01 to about 75 per cent, normally from about 0.05 to about 15 per cent, by weight of the composition. Carriers such as starch, sugar talc, commonly used synthetic and natural gums, water, and the like, may be used in such formulations. Binders such as polyvinylpyrrolidone and lubricants such as sodium stearate, may be used to form tablets. Disintegrating agents such as sodium bicarbonate may also be included in tablets.

Although relatively small quantities of the active materials of the invention, even as low as 5.0 milligrams, may be used in cases of administration to subjects having a relatively low body weight, unit dosages are preferably five milligrams or above and preferably 25, 50, or 100 milligrams, or even higher, depending of course upon the subject treated and the particular result desired, as will be apparent to one skilled in the art. Broader ranges appear to be 0.1 to 3000 milligrams per unit dose. The active agents of the invention may be combined for administration with other pharmacologically active agents such as natural or synthetic prostaglandins or analogues, antiseptics, spasmolytics, analgesics, tranquillizers, steroids or hormones, or the like, or with buffers, antacids or the like, and the proportion of the active agent or agents in the compositions may be varied widely. It is only necessary that the active ingredient of the invention constitutes an effective amount, i.e. such that a suitable effective dosage will be obtained consistent with the dosage form employed. Obviously, several unit dosage forms may be administered at about the same time. The exact individual dosages as well as daily dosages in a particular case will of course be determined according to well established medical and/or veterinary principles. As a rule, however, when used therapeutically, the present compounds may be administered in a quantity of 1 to 1000 milligrams per day and subject, divided in 1 or more doses, over a suitable period.

The following examples are intended to illustrate but not to limit the scope of the invention.

EXAMPLE 1

A solution of 5.12 g 1-(3,5-dimethyl-4-hydroxyphenyl)-2-(4-methoxyphenyl)-ethane in 20 ml dry pyridine is slowly (20 min) added with stirring to a solution of 0.46 ml phosphorus oxychloride in 10 ml dry pyridine at a temperature of −15° C. The reaction mixture is then kept at 0° C for 2 hours and then at room temperature during 50 hours. Water is then added and the resulting solution poured into a separatory funnel containing 150 ml 5 M hydrochloric acid and 150 ml ethyl acetate. The organic phase is separated and washed with water and saturated disodium sulphate solution and finally dried with anhydrous disodium sulphate. The solvent is removed by evaporation in vacuo and the residue purified by column chromatography on silica gel (ethyl acetate - methanol). The secondary phosphoric acid ester obtained in such a way is pure in thin-layer chomatography (TLC) and after evaporation to dryness in vacuo the free acid is transferred to the sodium salt by dissolving it in acetone - water and adding sodium hydroxide to a pH-value of about 5. Most of the acetone is removed in vacuo and the residue freeze-dried.

The ester obtained is sodium bis(4-(2-(4-methoxyphenyl)ethyl)-2,6-dimethylphenyl) phosphate and its structure is confirmed by NMR.

In substantially the same manner the following compounds are prepared:

sodium bis(4-(2-(4-methoxy-3,5-dimethylphenyl)ethyl)phenyl) phosphate
sodium bis(3-(2-(4-methoxy-3,5-dimethylphenyl)ethyl)phenyl) phosphate
sodium bis(4-(2-(4-methoxy-3,5-dimethylphenyl)ethyl)-2,6-dimethylphenyl) phosphate
(The phenols used as starting materials for the four compounds mentioned above are found in Ex. 21)
sodium bis(4-(1-ethyl-2-(4-methoxyphenyl)-1-butenyl)phenyl) phosphate from 3-(4-hydroxyphenyl)-4-(4-methoxyphenyl)-3-hexene
sodium bis(4-(2-(4-butoxyphenyl)-1-ethyl-1-butenyl)phenyl) phosphate from 3-(4-n-butoxyphenyl)-1-(4-hydroxyphenyl)-3-hexene (which is obtained according to C.A. 40 177[2])
sodium bis(2-(3-phenylpropyl)phenyl)phosphate from 1-(2-hydroxyphenyl)-3-phenyl propane.
sodium bis(4-(1-butoxy-1-phenylmethyl)phenyl)-phosphate from 1-butoxy-1-(4-hydroxyphenyl)-1-phenyl-methane.
sodium bis(4-(3-(2,4-dimethoxyphenyl)propyl)phenyl) phosphate from 1-(2,4-dimethoxyphenyl)-3-(4-hydroxyphenyl)propane
sodium bis(4-(3-(2,4,6-trimethoxyphenyl)propyl)phenyl) phosphate from 1-(4-hydroxyphenyl)-3-(2,4,6-trimethoxyphenyl)-propane
(The last two phenols are prepared by hydrogenation of the corresponding ketones which are obtained from the Hoesch reaction between 3-(4-hydroxyphenyl)propionitrile and 1,3-dimethoxybenzene and 1,3,5-trimethoxybenzene, respectively.

EXAMPLE 2

The monobenzoate of diethylstilbestrol (25.5 g) obtained according to Example 19 is dissolved in dry pyridine (90 ml). At a temperature of about −10° C this solution is added with stirring during half an hour to a solution of phosphorus oxychloride (3 ml, 0.033 mole) in dry pyridine (25 ml). The resulting reaction mixture is held at −10° C for an addition hour and is then allowed to rise to room temperature. Next day the clear solution is poured on crushed ice (100 g) and then most of the pyridine is removed in vacuo. The residue is dissolved in ethanol at the steambath and poured into a mixture of 2 M hydrochloric acid (250 ml) and ice (100 g). The resulting precipitate (27 g) is collected with filtration, washed with water and dried in vacuo. This product is dissolved in ether (300 ml) and left in a refrigerator to the next day, when a small precipitation is filtered off whereupon the ether is removed in vacuo. The residue is dissolved in ethanol (250 ml) and 5 M sodium hydroxide (100 ml) is added. The resulting solution is left at room temperature for 24 hours (hydrolysis of the benzoate groups). Then most of the ethanol is removed in vacuo, water (200 ml) is added and the pH adjusted to 5 with 5 N hydrochloric acid. After adding acetate buffer (0.4 M, pH 5, 100 ml) the resulting reaction mixture is boiled for 15 hours (hydrolysis of primary phosphoric acid esters of diethylstilbestrol). After cooling the resulting precipitate (15 g) is collected by filtration, washed with water and dried. It is then dissolved in ethyl acetate (200 ml) and cyclohexylamine (3 ml) is added. The cyclohexylammonium bis(diethylstilbestrol) phosphate obtained (9 g) is recrystallized from acetone-ether (1:1, 400 ml). This compound is pure in thin-layer chromatography (TLC) using butanol saturated with water.

Ethylacetate and 5 M hydrochloric acid is added to the cyclohexylamine salt and the mixture vigorously shaken. When the compound is dissolved, the ethyl acetate solution is separated, washed with water and the solvent removed in vacuo. The residue is dissolved in acetone-water with sodium hydroxide to a pH-value of about 5. Most of the acetone is removed in vacuo and the remaining water solution freeze-dried.

The sodium bis(diethylstilbestrol) phosphate obtained is pure in TLC and its structure is confirmed by NMR.

In substantially the same manner, starting with the monobenzoates (see Ex. 20 and 19) the following compounds are prepared:
sodium bis-dienestrol phosphate
sodium bis(4-(1-ethyl-2-(4-hydroxyphenyl)butyl)-phenyl) phosphate
sodium bis-hexestrol phosphate
sodium bis(4-(1-(4-hydroxy-3,5-dimethylphenyl)-1-methylethyl)-2,6-dimethylphenyl) phosphate sodium bis(4-(4-hydroxy-3,5-dimethylphenyl)methyl)-2,6-dimethylphenyl) phosphate.

sodium bis(4-1-(4-hydroxy-3,5-dichlorophenyl)-1-methylethyl)-2,6-dichlorophenyl) phosphate sodium bis(4-(1-ethyl-1-(4-hydroxyphenyl)propyl)-phenyl) phosphate sodium bis(4-(1-(4-hydroxyphenyl)-1-methylethyl)-phenyl) phosphate sodium bis(4-(1-(4-hydroxyphenyl)-2-phenylethenyl)phenyl) phosphate sodium bis(3-ethyl-4-(2-(2-ethyl-4-hydroxyphenyl)ethyl)phenyl) phosphate sodium bis(4-(1-ethyl-3-(4-hydroxyphenyl)pentyl)phenyl) phosphate sodium bis(2-ethyl-3-2-(2-ethyl-3-hydroxyphenyl)ethyl)phenyl) phosphate sodium bis(2-allyl-4-(1-(3-allyl-4-hydroxyphenyl)-1-methylethyl)phenyl) phosphate sodium bis(2-butyl-4-(1-(3-butyl-4-hydroxyphenyl)-1-methylethyl)phenyl) phosphate sodium bis(2-fluoro-4-(1-(3-fluoro-4-hydroxyphenyl)-1-methylethyl)phenyl) phosphate

EXAMPLE 3

To a solution of 5.1 g 1-(4-hydroxyphenyl)-2-(3,5-dimethyl-4-methoxyphenyl)-ethane in 20 ml dry pyridine, 2.66 g of freshly distilled trichloroethyl phosphorodichloridate is added with stirring at a temperature of about −15° C. The reaction mixture is then allowed to rise to room temperature and kept at this temperature for 70 hours. Water is then added and the reaction mixture poured into a separatory funnel containing a mixture of ethyl acetate and 2M hydrochloric acid. The organic phase is washed with 0.5 M hydrochloric acid, water, 0.5 M sodium bicarbonate solution and finally with water. After drying over anhydrous sodium sulphate the ethyl acetate is evaporated in vacuo. An oil is obtained which is dissolved in 50 ml of a mixture of pyridine-acetic acid (8:2). At a temperature of 0° C activated Zn (J. Biol. Chem. 230 (1958) 447; J. Org. Chem. 29 (1964) 2048) is added with stirring. After 0.5 hour the temperature is allowed to rise to room temperature and the mixture is left to the next day. The reaction mixture is then filtered and the clear solution poured into a mixture of 2 M hydrochloric acid and ethyl acetate. The organic phase is washed with water, dried and evaporated to dryness. The residue is dissolved in acetone - water and 2 M sodium hydroxide added to a pH value of about 5. Most of the acetone is removed in vacuo and the remaining solution freeze-dried. The sodium salt obtained is identical with that prepared in Ex. 4.

EXAMPLE 4

1-(4-hydroxyphenyl)-2-(3,5-dimethyl)-4-methoxyphenyl)ethane (5.1 g) and N-methylphosphoramidic dichloride (1.5 g) are dissolved in dry benzene (20 ml). The solution is refluxed, and triethylamine (2 g) dissolved in dry benzene (10 ml) is added dropwise with stirring. The reaction mixture is refluxed for 3 hours.

The benzene solution is cooled, washed with 0.5 M hydrochloric acid, water and 0.5 M sodium bicarbonate. The organic phase is dried with magnesium sulphate, filtered and the benzene is evaporated. The residue is dissolved in 200 ml of a mixture of 1 part 1 M sulfuric acid and 3 parts of acetone and refluxed for 4 hours.

The acetone is evaporated under vacuum, and the aqueous residue extracted with ethyl acetate. The organic phase is washed with water and dried with magnesium sulphate and then evaporated under vacuum. The residue is dissolved in methanol and pH is adjusted to 7 with 2 M sodium hydroxide. The methanol is evaporated under vacuum and the substance left is dissolved in acetone and precipitated with ether. The precipitate (4 g) is:

sodium bis(4-(2-(4-methoxy-3,5-dimethylphenyl)ethyl)phenyl) phosphate showing one spot in TLC (silica gel, n-butanol - water) and its structure is confirmed by NMR.

In substantially the same manner the sodium salt is obtained of sodium bis 4-(1-methyl-1-phenyl-ethyl)phenyl) phosphate from 2-(4-hydroxy-phenyl)-2-phenyl-propane.

EXAMPLE 5

To a solution of 3.2 g of the primary phosphoric acid ester of diethylstilbestrol monobenzoate (prepared according to Ex. 21 and dried by several evaporations in vacuo with dry pyridine) in 30 ml dry pyridine, triethylamine (2.02 g) and 1,3,5-triisopropylbenzene-sulphonyl chloride (4.46 g) are added. The mixture is kept for 2 hours at room temperature, the monobenzoate of diethylstilbestrol (2.7 g) is added and the reaction mixture left for 70 hours at room temperature. Water is then added and the resulting solution poured into an excess of 2 M hydrochloric acid. The resulting precipitate is collected by filtration, washed with water and then dissolved in ethanol - water with an excess of sodium hydroxide. Next day the pH-value is adjusted to about 5 with hydrochloric acid, half the volume of an 0.4 M acetate buffer (pH 5) added and the resulting mixture boiled for 15 hours so that all unreacted monophosphate is hydrolyzed. Free diethylstilbestrol is then removed by extraction with ether. By precipitation with hydrochloric acid a product is obtained which is dissolved in ethanol and purified in preparative thinlayer chromatography (SiO$_2$). Bis-diethylstilbestrol phosphate is extracted with pyridine - water (1:1). The solution is treated with hydrochloric acid and the free acid precipitated is then dissolved in acetone - water with sodium hydroxide to pH 5. Most of the acetone is removed in vacuo and the remaining solution freeze-dried. The sodium salt of bis-diethylstilbestrolphosphate obtained with this method is pure in TLC and corresponds in every respect with that obtained according to Ex. 2.

In substantially the same manner starting from
4-(2-phenylethyl)phenyl dihydrogen phosphate and
2-(4-hydroxyphenyl)-2-phenyl-propane the
sodium 4-(2-phenylethyl)phenyl 4-(1-methyl-1-phenyl-ethyl)phenyl phosphate is obtained.

EXAMPLE 6

4.5 g of the primary phosphoric acid ester of diethyl-stilbestrol-monobenzoate (prepared according to Ex. 21) and dried by evaporation in vacuo with dry pyridine), is dissolved in 15 ml dry pyridine. Trichloroacetonitrile (14.4 g) and ethanol (0.92 g) is added and the reaction mixture heated to 90° for 3 hours. After evaporation in vacuo the residue is dissolved in 1 M sodium hydroxide, filtered free from trichloroacetamido and then 2 volumes of ethanol are added. The solution is left at room temperature during the night. Next day most of the ethanol is evaporated in vacuo and the same volume of 5 M hydrochloric acid saturated with sodium chloride added. An oil separated which is purified by chromatography on silica gel with ethyl acetate - ethanol. After evaporation an oil is obtained which is diethylstilbestrol ethyl hydrogen phosphate pure in TLC. It is dissolved in water with 2 M sodium hydroxide to a pH value of about 5 and the solution freeze-dried. The structure of the sodium salt obtained is confirmed in NMR.

Exchange of the ethanol in the example above against 2 g cyclohexanol gives the sodium diethylstilbestrol cyclohexyl phosphate.

In substantially the same manner but directly precipitating the solution obtained, after trichloroacetamide has been removed, with hydrochloric acid saturated with sodium chloride, the following compounds are obtained from primary phosphoric acids described in Ex. 21.

- sodium ethyl 4-(2-(4-methoxy-3,5-dimethylphenyl)ethyl)phenyl phosphate
- sodium ethyl 4-(2-(4-methoxyphenyl)ethyl)-2,6-dimethylphenyl phosphate
- sodium ethyl 4-(2-(4-methoxy-3,5-dimethylphenyl)ethyl)2,6-dimethylphenyl phosphate
- sodium 4-methyl-pentyl 4-(2-(phenyl)ethyl)phenyl phosphate (using 2-methylpentanol instead of ethanol.)
- sodium 2-ethyl-butyl 4-(3-(2,4,6-trimethoxyphenyl)propyl)phenyl phosphate (using 2-ethyl-1-butanol instead of ethanol.)
- sodium 4-tert.-butyl-cyclohexyl 4-(3-(2,4,6-trimethoxyphenyl)propyl)phenyl phosphate (using 4-tert.-butyl-cyclohexanol instead of ethanol.)

EXAMPLE 7

A solution of 2.6 g 1-(3,5-dimethyl-4-hydroxyphenyl)-2-(3,5-dimethyl-4-methoxyphenyl)-ethane in 50 ml pyridine is slowly added (45 min) with stirring to a solution of 12.6 g phenylphosphorodichloridate in 50 ml dry pyridine at a temperature of −10° C. After an additional hour the temperature is held at 0° C for 1 hour and at room temperature to the next day. The reaction mixture is poured on crushed ice (50 g) and the resulting solution evaporated in vacuo to a volume of about 50 ml. This solution is then poured into a mixture of conc. hydrochloric acid (50 ml) and crushed ice (100 g). The precipitate is collected, dissolved in ethanol and precipitated with water. The precipitate is collected by filtration, washed with water and dissolved in acetone:aq., 1:4 with sodium hydroxide to a pH of about 5.0. The acetone is evaporated in vacuo and the solution freeze-dried. The sodium 2,6-dimethyl-4-(2-(3,5-dimethyl-4-methoxyphenyl)ethyl)phenyl phenyl phosphate obtained is pure in TLC. The structure is confirmed by NMR.

In substantially the same manner the following secondary phosphoric acid esters are prepared from substituted or unsubstituted aryl phosphorodichloridates and a monophenolic compound (given below). The different substituted or unsubstituted aryl phosphorodichloridates which are used as starting material will be clearly understood from the names of the endproducts mentioned below.

- sodium 3-(2-(3,5-dimethyl-4-methoxyphenyl)ethyl)phenyl phenyl phosphate from 1-(3,5-dimethyl-4-methoxyphenyl)-2-(3-hydroxyphenyl)ethane
- sodium 4-(2-(3,5-dimethyl-4-methoxyphenyl)ethyl)phenyl phenyl phosphate from 1-(3,5-dimethyl-4-methoxyphenyl)-2-(4-hydroxyphenyl)ethane
- sodium 2,6-dimethyl-4-(2-(4-methoxyphenyl)ethyl)phenyl phenyl phosphate
- sodium 4-(2-(4-methoxyphenyl)ethyl)-2,6-dimethylphenyl 4-tert. butylphenyl phosphate
- sodium 4-(2-(4-methoxyphenyl)ethyl)-2,6-dimethylphenyl 4-chlorophenyl phosphate
- sodium 3,5-dimethylphenyl 2,6-dimethyl-4-(2-(4-methoxyphenyl)ethyl)phenyl phosphate
- sodium 4-(2-(4-methoxyphenyl)ethyl)-2,6-dimethylphenyl 4-methoxyphenyl phosphate
- sodium 4-(2-(4-methoxyphenyl)ethyl)2,6-dimethylphenyl 2-nitrophenyl phosphate The last six phosphates are prepared from 1-(3,5dimethyl-4-hydroxyphenyl)-2-(4-methoxyphenyl)ethane

- sodium 4-(4-(4-methoxyphenyl)-3-hexen-3-yl)phenyl phenyl phosphate from 3-(4-hydroxyphenyl)-4-(4-methoxyphenyl)-3-hexene
- sodium 2-chloro-4-biphenylyl phenyl phosphate from 2-chloro-4-phenylphenol
- sodium 4-(4-(4-ethoxycarbonylmethoxyphenyl)-3-hexen-3-yl)phenyl phenyl phosphate from 3-(4-hydroxyphenyl)-4-(4-ethoxycarbonylmethoxyphenyl)-3-hexene (obtained from the monobenzoate of diethylstilbestrol and the ethylester of bromoacetic acid)

- sodium 2-nitro-4-biphenylyl phenyl phosphate from 2-nitro-4-phenylphenol
- sodium 4-(3-(2,4-dimethoxyphenyl)propyl)phenyl phenyl phosphate from 1-(2,4-dimethoxyphenyl)-3-(4-hydroxyphenyl)propane
- sodium 4-biphenylyl phenyl phosphate from 4-phenylphenol
- sodium 3-(3-(3,5-dimethyl-4-methoxyphenyl)propyl)phenyl phenyl phosphate from 1-(3,5-dimethyl-4-methoxyphenyl)-3-(3-hydroxyphenyl)propane (obtained by hydrogenation of the corresponding chalcone prepared by alkaline condensation of m-hydroxybenzaldehyde and 3,5-dimethyl-4-methoxy-acetophenone)

- sodium 2-biphenylyl phenyl phosphate from 2-phenylphenol
- sodium 4-(3-phenylpropyl)phenyl phenyl phosphate from 1-(4-hydroxyphenyl)-3-phenylpropane
- sodium 2,6-dibromo-4-(4-bromophenyl)phenyl phenyl phosphate from 4-(4-bromophenyl)-2,6-dibromphenol
- sodium 4-(3-(4-fluorophenyl)propyl)phenyl phenyl phosphate from 1-(4-fluorophenyl)-3-(4-hydroxyphenyl)propane (obtained by hydrogenation of the corresponding chalcone, prepared by alkaline condensation of 4-hydroxybenzaldehyde and 4-fluoroacetophenone)

- sodium 4-(2,2-diphenylethenyl)phenyl phenyl phosphate and
- sodium 3,5-dimethylphenyl 4-(2,2-diphenylethenyl)phenyl phosphate from 1,1-diphenyl-2-(4-hydroxyphenyl)ethene (obtained after demethylation of the corresponding methylether with $BBr_3$)

- sodium 4-(2,2-diphenylethyl)phenyl phenyl phosphate and sodium 3,5-dimethylphenyl 4-(2,2-diphenylethyl)-phenyl phosphate from 1.1-diphenyl-2-(4-hydroxyphenyl)ethane
(obtained by hydrogenation of the corresponding ethene derivative)

sodium 2-brom-4-biphenylyl phenyl phosphate from 2-brom-4-phenylphenol sodium 2,6-dimethoxy-3',4',5'-trimethoxy-4-biphenylyl phenyl phosphate from 2,6-dimethoxy-4-(3,4,5-trimethoxyphenyl) phenol sodium 2,6-dichloro-4biphenylyl phenyl phosphate from 2,6-dichloro-4-phenylphenol sodium 3,5-dimethylphenyl 4-styrylphenyl phosphate from 4-hydroxystilbene sodium 3,5-dimethylphenyl 4-(2-phenylethyl)phenyl phosphate from 1-(4-hydroxyphenyl)-2-phenylethane sodium 3,5-dimethylphenyl 4-(1-methoxy-1-phenylmethyl)phenyl phosphate from 1-(4-hydroxyphenyl)-1-methoxy-1-phenylmethane
(obtained by methylation of 4-acetoxybenzhydrol, followed by deacetylation)

sodium 2-(phenylmethyl)phenyl 4-fluorophenyl phosphate from 1-(2-hydroxyphenyl)-2-phenylmethane sodium 4(1-phenyl-1-methylethyl)phenyl 1-naphthyl phosphate sodium 4-(1-phenyl-1-methylethyl)phenyl 2-naphthyl phosphate sodium 4-(1-phenyl-1-methylethyl)phenyl 2-isopropylphenyl phosphate sodium 4-(1-phenyl-1-methylethyl)phenyl 4-isopropylphenyl phosphate sodium 4-(1-phenyl-1-methylethyl)phenyl 3-biphenylyl phosphate sodium 4-(1-phenyl-1-methylethyl)phenyl 2-biphenylyl phosphate The last six phosphates are prepared from 2-(4-hydroxyphenyl)-2-phenylpropane sodium 4-(2-cyanophenylmethyl)phenyl 3-trifluoromethylphenyl phosphate from 1-(2-cyanophenyl)-1-(4-hydroxyphenyl)methane sodium 4-(2-methoxycarbonylphenylmethyl)phenyl 4-methoxyphenyl phosphate from 1-(2-methoxycarbonylphenyl)-1-(4-hydroxyphenyl)methane sodium 4-(2-N,N-dimethylcarbamoylphenylmethyl)-phenyl 3-nitrophenyl phosphate from 1-(2-N,N-dimethylcarbamoylphenyl)-1-(4-hydroxyphenyl)methane sodium 4-(2-cyclohexyl-2-phenylethenyl)phenyl 2-methylphenyl phosphate from 1-cyclohexyl-1-phenyl-2-(4-hydroxyphenyl)ethene
(obtained by dimethylation (BBr$_3$) of its methylether)

sodium 4-(4-trifluoromethylphenylmethyl)phenyl 2,6-dimethoxyphenyl phosphate from 1-(4-trifluoromethylphenyl)-1-(4-hydroxyphenyl)methane
(obtained by hydrogenation of the corresponding benzophenone which is prepared by Friedel-Craft reaction between phenol and 4-trifluoromethylbenzoylchloride)

sodium 4'-carboxymethyl-4-biphenylyl 3-ethyl-5-methyl-phenyl phosphate from 4-(4-carboxymethylphenyl)phenol
(obtained from 4-methoxy biphenyl which is converted to the corresponding 4'-acetylderivative (Friedel-Craft reaction with acetylchloride) which after a Willgerodt rearrangement and demethylation gives the desired phenol).

sodium 4-(2,2-bis(4-methoxyphenyl)ethenyl)phenyl 3,5-dimethylphenyl phosphate obtained from 1,1-bis(4-methoxyphenyl)-2-(4-hydroxyphenyl) ethene sodium 4-(2,2-bis(4-chlorophenyl)ethenyl)phenyl 3,5-dimethylphenyl phosphate obtained from 1,1-bis(4-chlorophenyl)-2-(-hydroxyphenyl) ethene The last two phenols mentioned above are prepared from 4,4'-disubstituted benzophenones and the Grignard reagens obtained from 4-benzoxybenzylchloride, followed by hydrogenation to remove the benzylgroups and a treatment with polyphosphoric acid to obtain the unsaturated compounds.

sodium 4-(3-(2,4,6-trimethoxyphenyl)propyl)phenyl 3,5-dimethylphenyl phosphate from 1-(4-hydroxyphenyl)-3-(2,4,6-trimethoxyphenyl)propane.

EXAMPLE 8

A solution of 4.5 g monobenzoate of diethylstilbestrol dissolved in 75 ml dry pyridine is slowly added (1 hour) with stirring to a solution of 15.2 g phenyl phosphorodichloridate in 75 ml dry pyridine at a temperature of −10° C. After an additional hour the temperature is held at 0° C for 1 hour and then at room temperature to the next day. The reaction mixture is poured on 75 g crushed ice and the resulting solution evaporated in vacuo to a volume of about 50 ml. The precipitate obtained is collected, dissolved in ethanol and poured into 2 M hydrochloric acid (300 ml). The precipitate is redissolved in ethanol (200 ml) and 100 ml 1 M sodium hydroxide added. This solution is left to the next day (hydrolysis of the benzoate group). The pH-value is adjusted to about 7 with hydrochloric acid and the solution evaporated in vacuo until a small precipitate is formed. This is dissolved by adding sodium hydroxide solution and the clear solution poured into 5 M hydrochloric acid (100 ml). The precipitate is collected by filtration washed with water and directly recrystallized from ethanol - water (1:3). Diethylstilbestrol phenyl hydrogen phosphate so obtained is pure in TLC. It is dissolved in acetone:aq., 1:4 with sodium hydroxide to a pH about 5.0. The acetone is evaporated in vacuo and the solution is freeze-dried. The structure of the sodium salt obtained is confirmed by NHR.

In substantially the same manner the following secondary phosphoric acid esters are prepared from substituted or unsubstituted aryl phosphordichloridates and monobenzoates (see Ex. 19 and 20). The different substituted or unsubstituted arylphosphordichloridates which are used as starting material will be clearly understood from the names of the end-products mentioned below.

sodium 4-(1-ethyl-2-(4-hydroxyphenyl)butyl)phenyl phenyl phosphate sodium 4-(1-ethylidene-2-(4-hydroxyphenyl)-2-butenyl)phenyl phenyl phosphate sodium 4-(1-(4-hydroxy-3,5-dimethylphenyl)-1-methylethyl)-2,6-dimethylphenyl phenyl phosphate sodium 4-(1-ethyl-1-(4-hydroxyphenyl)propyl)phenyl phenyl phosphate sodium 4-(1-(4-hydroxyphenyl)-1-methylethyl)phenyl 2-chlorophenyl phosphate sodium 3,5-dimethoxyphenyl 4-(4-(4-hydroxyphenyl)butyl)phenyl phosphate sodium 4-(4-(4-hydroxyphenyl)-3-hexen-3-yl)phenyl 3,5-dimethylphenyl phosphate sodium 4-(1-(4-hydroxyphenyl)-1-methylethyl)phenyl 3,5-dimethylphenyl phosphate sodium 4-(4-hydroxy-3,5-dimethylphenyl)-2,6-dimethylphenyl phenyl phosphate sodium 4-(3-(4-hydroxyphenyl)propyl)phenyl phenyl phosphate The following three phosphates are prepared from the monoacetates mentioned below which are obtained by partial deacetylation (methanol-water, $K_2CO_3$) of the corresponding diacetates. The dihydroxy compounds are prepared by reduction of the corresponding 4-hydroxy benzophenones and 4-hydroxy-dihydrochalcone respectively.

sodium 4-(3-hydroxy-3-phenylpropyl)phenyl 3,5-dimethylphenyl phosphate from 1-acetoxy-1-phenyl-3(4-hydroxyphenyl)propane.

sodium 4-(1-hydroxy-1-phenylmethyl)phenyl 3,5-dimethylphenyl phosphate from 1-acetoxy-1-(4-hydroxyphenyl)-1-phenylmethane sodium 4-(1-butyl-1-hydroxy-1-phenylmethyl)phenyl 3,5-dimethylphenyl phosphate from 1-acetoxy-1-butyl-1-(4-hydroxyphenyl)-1-phenyl-methane sodium 4-(1-(4-hydroxyphenyl)-2-(3-methylphenyl)ethenyl)phenyl 3,5-dimethylphenyl phosphate sodium 4-(1-(4-hydroxyphenyl)-2-(4-fluorophenyl)ethenyl)phenyl 3,5-dimethylphenyl phosphate sodium 4-(1-(4-hydroxyphenyl)-2-(4-trifluoromethylphenyl) ethenyl)phenyl 3,5-dimethylphenyl phosphate

EXAMPLE 9

4.75 g of 2-(4-benzoyloxy-3-dimethylaminomethyl-5-methylphenyl)-2-(3-dimethylaminomethyl-4-hydroxy-5-methylphenyl)propane (see Ex. 20) is dissolved in 70 ml of dry pyridine, and this solution is slowly added (1 hour) with stirring to a solution of 12 g 3,5-dimethylphenylphosphorodichloridate in 75 ml dry pyridine at −10° C. After another hour at −10° C and 1 hour at room temperature the reaction mixture is poured on crushed ice. The next day the solution obtained is evaporated in vacuo, to remove pyridine, water is added and the separated oil is washed with water. The oil is dissolved in ethanol (200 ml) and 100 ml 1 M sodium hydroxide added. This solution is left to the next day (hydrolysis of the benzoate group). The pH-value is adjusted to about 7 with hydrochloric acid and the solution evaporated in vacuo to remove the ethanol, and the remaining water solution is freeze-dried. This product is treated with dry acetone and filtered. The clear acetone solution is evaporated in vacuo, the residue dissolved in water and freeze-dried giving sodium 2-dimethylaminomethyl-4-(1-(3-dimethylaminomethyl-4-hydroxy-5-methylphenyl)-1-methylethyl)-6-methylphenyl) 3,5-dimethylphenyl phosphate.

EXAMPLE 10

4-hydroxy diphenylmethane (1.21 g 6.6 mmoles) tetrahydrofurane (6 ml), pyridine (0.54 ml, 6.7 mmoles) and 2-chloromethyl-4-nitro-phenylphosphorodichloridate (0.91 g, 3 mmoles) is kept for 24 hours at room temperature, and then 1 hour at 60° C. After cooling pyridine hydrochloride is filtered off and the solvent is evaporated. The residue is dissolved in benzene and chromatographed on a silica gel column. The tertiary phosphate ester is eluated with benzene and evaporated. Yield 0.55 g.

0.5 g of the tertiary phosphate is dissolved in 10 ml of pyridine. Water is added until the solution becomes opalescent. The solution is kept at room temperature for 2 days and then heated at 80° C for 8 hours. The reaction is followed on TLC (water-n - BuOH). The reaction mixture is poured into 20 ml of ethylacetate and 0.2 M hydrochloric acid. The filtered ethylacetate solution is evaporated in vacuo. Methanol is added and the undissolved is filtered off. The pH of the solution is adjusted to 5 with 5 M sodium hydroxide, evaporated, dissolved in acetone and precipitated with ether. Yield 0.19 g of sodium bis(4-phenylmethyl)phenyl)phosphate.

EXAMPLE 11

3.6 g of 2-chloromethyl-4-nitrophenyl p-tolyl hydrogen phosphate (Tetrahedron Letters No. 40, p. 3505–3508, 1970), 4.6 g of 1-(4-hydroxyphenyl)-2-(3,5-dimethyl-4-methoxyphenyl)ethane and 4 ml of dry pyridine is kept at room temperature for 2 days and then heated at 90° C over night. 30 ml of absolute ethanol is added and the mixture is stirred at room temperature for several minutes.

A yellow precipitate of 1-(2'-hydroxy-5'-nitro-benzyl)pyridinium chloride is filtered and washed with two 20 ml portions of absolute ethanol.

The combined alcoholic filtrate and washings are evaporated to dryness under reduced pressure. The residue is poured into a mixture of 25 ml of 2 M hydrochloric acid and ethyl acetate. Water is added to the organic layer and pH is adjusted to 5 with 1 M sodium hydroxide. The aqueous layer is freeze-dried giving sodium 4-(2-(3,5-dimethyl-4-methoxyphenyl)ethyl)-phenyl, 4-methylphenyl phosphate.

In substantially the same manner the following compound is obtained.

sodium 4-benzylphenyl 4-(1-methyl-1-phenylethyl)-phenyl phosphate from 4-benzylphenyl 2-chloromethyl-4-nitrophenyl hydrogen phosphate (which is obtained in substantially the same manner as the corresponding p-tolyl-derivative described in Tetrahedron Letters No. 40, p. 3505–3508, 1970) and 4-(1-methyl-1-phenylethyl)phenol.

EXAMPLE 12

Acetic anhydrid (5.1 g, 50 mmoles) is added to a solution of sodium 4-(1-(4-hydroxy-3,5-dimethylphenyl)-1-methylethyl)-2,6-dimethylphenyl phenyl phosphate (2.31 g, 5 mmoles) in 20 ml dry pyridine. The mixture is kept at room temperature for 18 hours and poured on 200 g of ice-water. The pH of the mixture is adjusted to 1 with 1 M hydrochloric acid at 0° C. The aqueous phase is discarded. The residue is ground with ice-water and dissolved in acetone:aq., 1:3. The pH of the solution is adjusted to 5. The acetone is evaporated in vacuo and the remaining syrup precipitate which solidifies on standing is sodium 4-(1-(4-acetoxy-3,5-dimethylphenyl)-1-methylethyl)-2,6-dimethylphenyl phenyl phosphate. The structure is confirmed by NMR.

In substantially the same manner the corresponding esters are obtained from starting materials found in Ex. 8, 15, and 17 sodium 4-(1-(3,5-dimethyl-4-propionyloxyphenyl)-1-methylethyl)-2,6-dimethylphenyl phenyl phosphate sodium 4-(1-ethyl-2-(4-acetoxyphenyl)-1-butenyl)-phenyl phenyl phosphate sodium 4-(1-(4-butyryloxyphenyl)-1-methylethyl)-phenyl 3,5-dimethylphenyl phosphate sodium 4-(2-N,N-dimethylcarbamoylphenylmethyl)-phenyl 3-acetamidophenyl phosphate sodium 4-acetoxyphenyl 4-(1-phenyl-1-methylethyl)phenyl phosphate sodium 4-(1-phenyl-1-methylethyl)phenyl 4-pivaloyloxyphenyl phosphate sodium 4-(1-acetoxy-1-phenylmethyl)phenyl 3,5-dimethylphenyl phosphate

EXAMPLE 13

The sodium bis-diethylstilbestrol phosphate from Ex. 2 (2 g, 0.03 mole) is dissolved in dry pyridine (35 ml). This solution is added with stirring during 15 minutes to a solution of phosphorus oxychloride (1.6 ml, 0.018 mole) in dry pyridine (50 ml) kept at about −10° C. The resulting reaction mixture is kept at −10° C for an additional hour and is then allowed to rise to room temperature. After one hour the clear solution is poured on crushed ice (50 g) and most of the pyridine is removed in vacuo. The solution obtained is then poured in cold 5 M hydrochloric acid (50 ml) and the resulting precipitate collected by filtration and washed with cold water. The residue is dissolved in water with 2 M sodium hydroxide to a pH-value of about 5 and the solution freeze-dried. The trisodium salt of bis(0'-(dihydroxy-phosphinyl)-diethylstilbestrol) hydrogen phosphate obtained in this way gives the sodium bis-diethylstilbestrol phosphate (checked by TLC) and the calculated amount of free phosphoric acid when its solution is kept at 100° C for 20 hours at pH 5 (acetate-buffer).

In substantially the same manner the following compound is obtained.

The disodium salt of 4-dihydroxyphosphinyloxyphenyl 4-(1-phenyl-1-methylethyl)phenyl hydrogen phosphate from sodium 4-hydroxyphenyl 4-(1-methyl-1-phenylethyl) phenyl phosphate (see Ex. 16).

EXAMPLE 14

To a mixture of 22.3 g of diethylstilbestrol phenyl hydrogen phosphate (see Ex. 8) and 1000 ml of 0.22 M sodium ethoxide kept under nitrogen, 5.7 g of chloroacetic acid in 50 ml anhydrous ethanol is added dropwise with stirring and the mixture being kept boiling. After all of the acid is added the refluxing is continued for 1 hour. The reaction mixture is cooled and sodium chloride is removed by filtration. The solvent is evaporated in vacuo, and the residue is dissolved in water, acidified with 2 M hydrochloric acid and extracted with ethyl acetate. The organic layer is washed with saturated sodium sulphate solution. Water is added and pH adjusted to 7 with 2 M sodium hydroxide. The water layer is freeze-dried giving disodium 4-(4-(4-carboxylatemethoxyphenyl)-3-hexen-3-yl)phenyl phenyl phosphate.

EXAMPLE 15

4.4 g of 4-(2-N,N-dimethylcarbamoylphenyl-methyl)phenyl 3-nitro-phenyl hydrogen phosphate (see Ex. 7) in 100 ml 0.1 M sodiumethoxide is hydrogenated at room temperature and atmospheric pressure with 0.5 g of 10% Pd/C as catalyst. The reaction almost stops when the calculated amounts of hydrogen has been absorbed. The catalyst is removed by filtration and the solvent is evaporated. The residue is precipitated with ether. Yield 3.2 g of sodium 4-(2-N,N-dimethylcarbamoylphenylmethyl)phenyl 3-aminophenyl phosphate.

In substantially the same manner the following secondary phosphoric acid ester is obtained:

sodium 2-amino-4-biphenylyl phenyl phosphate from sodium 2-nitro-2-biphenylyl phenyl phosphate (see Ex. 7)

sodium 4-(1-(4-hydroxyphenyl)-2-(3-methylphenyl)ethyl)phenyl 3,5-dimethylphenyl phosphate sodium 4-(1-(4-hydroxyphenyl)-2-(4-fluorophenyl)ethyl)phenyl 3,5-dimethylphenyl phosphate sodium 4-(1-(4-hydroxyphenyl)-2-(4-trifluoromethylphenyl)ethyl)phenyl) 3,5-dimethylphenyl phosphate (The last three esters mentioned above are obtained from the corresponding ethene derivatives, see Ex. 10).

EXAMPLE 16

To a solution of 20 g 1,4-phenylenyl-bis-phosphorodichloridate in 300 ml of dry pyridine, a solution of 3.7 g of the monobenzoate of diethylstilbestrol in 50 ml of dry pyridine is slowly added with stirring at 0° C. After additional 2 hours at 0° C the temperature is held at room temperature to the next day. The reaction mixture is poured into crushed ice and the resulting solution evaporated in vacuo to remove most of the pyridine. The solution obtained (100 ml) is poured into 5 M hydrochloric acid (100 ml). The precipitate is dissolved in ethanol (200 ml) and 100 ml 1 M sodium hydroxide added. This solution is left to the next day (hydrolysis of the benzoate group). The pH-value is adjusted to about 7 with hydrochloric acid and the solution evaporated in vacuo to about 75 ml. This solution is poured into 50 ml 5 M hydrochloric acid and the precipitate collected by filtration and washed with a small amount of cold water and then dissolved in water with sodium hydroxide to a pH-value of about 5 and the solution freeze-dried.

The structure of the disodium salt of 4-dihydroxyphosphinyloxyphenyl diethylstilbestrol hydrogen phosphate obtained is confirmed by NMR.

In substantially the same manner the following compounds are obtained.

disodium 4-dihydroxyphosphinyloxyphenyl 4-(1-phenyl-1-methylethyl)phenyl hydrogen phosphate

EXAMPLE 17

To a solution of 34 g 1,4-phenylenyl-bis-phosphorodichloridate in 500 ml of dry pyridine, 4.2 g 2-phenyl-2-(4-hydroxyphenyl)propane in 50 ml of dry pyridine is added dropwise with stirring at 0° C. After additional 2 hours at 0° C the temperature is held at room temperature to the next day. The reaction mixture is poured into crushed ice. The solution is then evaporated in vacuo to remove most of the pyridine, water is added and pH is adjusted to 5 with 5 M sodium hydroxide and 75 ml 0.4 M acetate buffer (pH 5) is added. The solution (about 300 ml) is kept at 100° C 15 hours. Next day water is added and the mixture is steam distilled. pH is then adjusted to 1 and the mixture is extracted with ethylacetate.

The organic phase is washed with water, dried with disodium sulphate, filtered and evaporated in vacuo. The residue is shaken with 50 ml chloroform and the chloroform solution filtered. Water is added to this solution and pH is adjusted to 5 with 1 M sodium hydroxide and the water solution collected and freeze-dried.

The product obtained is sodium 4-hydroxyphenyl 4-(1-methyl-1-phenylethyl)phenyl phosphate. The structure is confirmed by NMR.

EXAMPLE 18

2 g of sodium bis 4-(1-methyl-1-phenyl-ethyl)phenyl) phosphate is dissolved in 150 ml water and 5 ml 50% solution is calciumchloride in water is added. The precipitate formed is collected by filtration, washed with water and dried in vacuo. The product obtained is the calcium salt of bis 4-(1-methyl-1-phenyl)-ethyl)-phenyl)hydrogen phosphate.

EXAMPLE 19

Diethylstilbestrol (3,4-bis(4-hydroxyphenyl)-3-hexene), 24 g is dissolved in ethanol (800 ml) and water (500 ml) is added. With vigorously stirring benzoyl chloride (10 ml, 0.087 mole) and 2.0 M sodium hydroxide (44 ml, 0.088 mole) are added simultaneously during one hour so that the pH-value is held between 7.5 – 8.5. The stirring is continued half an hour and the pH held about 8.0 with further addition of a small amount of 2.0 M sodium hydroxide (5 ml). Then water (100 ml) is added and the resulting reaction mixture is placed in a refrigerator during the night. Next day the precipitation is collected by filtration, washed with ethanol - water (1:1, 200 ml) and dried. The crude product (29 g) is dissolved in ether (600 ml) and filtered. The ether is then removed in vacuo and the residue boiled with ethanol (750 ml), undissolved product removed by filtration and the filtrate mixed with hot water (400 ml). From this solution the monobenzoate crystallizes on cooling. A further recrystallization from ethanol - water gives 17 g of the mono-benzoate of diethylstilbestrol with m.p. 137°–8° C.

In substantially the same manner the mono-benzoates of the following dihydroxy compounds are prepared:

Hexestrol (meso-3,4-bis(4-hydroxyphenyl)-hexane); 3,4-bis(4-hydroxyphenyl) hexane; 3,3bis(4-hydroxyphenyl)pentane; 2,2-bis(4-hydroxyphenyl) propane; 2,2-bis(4-hydroxyphenyl) styrene; 1,2-bis(2-ethyl-4-hydroxyphenyl)ethane, 1,2-bis(2-ethyl-3-hydroxyphenyl) ethane; dienestrol (3,4-bis(4-hydroyphenyl)-2,4-hexadiane); 3,5-bis(4-hydroxyphenyl) heptane; 1,4-bis(4-hydroxyphenyl)-butane, 1,3-bis(4-hydroxyphenyl) propane, 2,2-bis (3-fluoro-4-hydroxyphenyl) propane, 2,2-bis(4-hydroxyphenyl)-3'-methyl styrene, 2,2-bis(4-hydroxyphenyl)-4'-fluorostyrene and 2,2bis(4-hydroxyphenyl)-4'-trifluoromethyl styrene.

EXAMPLE 20

2,2-bis(3,5-dimethyl-4-hydroxyphenyl)-propane (22.8 g) is dissolved in pyridine (400 ml). At a temperature of 0° C 9.6 ml benzoyl chloride is slowly added (10 min) with stirring. After 15 min the reaction mixture is poured into water (1000 ml). An oil separated and is dissolved in hot ethanol (300 ml). This solution is placed in a refrigerator to next day. The precipitate formed is filtered off and to the clear solution hot water (500 ml) is added during reflux. On cooling the monobenzoate crystallized and after recrystallization from ethanol - water 10 g of the monobenzoate of 2,2-bis(3,5-dimethyl-4-hydroxyphenyl)-propane with m.p. 153° C is obtained.

In substantially the same manner the monobenzoates of the following dihydroxy compounds are prepared:
bis(3,5-dimethyl-4-hydroxyphenyl) methane; 2,2-bis(3,5-dichloro-4-hydroxyphenyl) propane; 2,2-bis(3-allyl-4-hydroxyphenyl) propane, 2,2-bis(3-butyl-4-hydroxyphenyl) propane, 4,4'-dihydroxy-3,3',5,5'-tetramethyl-biphenyl, and 2,2-bis(3-dimethylaminomethyl-4-hydroxy-5-methylphenyl) propane (prepared by Mannich reaction from 2,2-bis(4-hydroxy-3-methylphenyl) propane, dimethylamine and formaldehyde).

EXAMPLE 21

The monobenzoate of diethylstilbestrol (27 g) obtained according to Example 19 is dissolved in dry pyridine (300 ml). This solution is then slowly (1 hour) added with stirring and at −10° C to a solution of 30 ml phosphorus oxychloride in 300 ml dry pyridine. After one hour at −10° C the temperature is allowed to rise to about +20° C and kept at this temperature for 2 hours. The reaction mixture is poured on ice (300 g) and evaporated in vacuo. The residue is dissolved in ethanol (300 ml) and poured into 2 M hydrochloric acid (600 ml). The precipitate is collected and dissolved in acetone (300 ml). By adding water the monophosphate separated, and it is then recrystallized from ethyl acetate-hexane (1:1) (1000 ml) to give the pure primary phosphoric acid ester of diethylstilbestrolmonobenzoate. In TLC (buthanol saturated with water) only one spot is obtained.

In substantially the same manner the following primary phosphoric acid esters are obtained:
4-(2-phenylethyl)phenyl dihydrogen phosphate from 1-phenyl-2-(4-hydroxyphenyl)ethane
4-(2-(4-methoxy-3,5-dimethylphenyl)ethyl)phenyl dihydrogen phosphate from 1-(3,5-dimethyl-4-methoxyphenyl)-2-(4-hydroxyphenyl)ethane
3-(2-(4-methoxy-3,5-dimethylphenyl)ethyl)phenyl dihydrogen phosphate from 1-(3,5-dimethyl-4-methoxyphenyl)-2-(3-hydroxyphenyl)ethane
4-(2-(4-methoxy-3,5-dimethylphenyl)ethyl)-2,6-dimethylphenyl) dihydrogen phosphate from 1-(3,5-dimethyl-4-methoxyphenyl)-2-(3,5-dimethyl-4-hydroxyphenyl)ethane.
4-(2-(4-methoxyphenyl)-ethyl)-2,6-dimethylphenyl dihydrogen phosphate from 1-(3,5-dimethyl-4-hydroxyphenyl)-2-(4-methoxyphenyl)-ethane.

The four phenols last mentioned above are prepared in substantially the same manner as described below for, the first one, 1-(3,5-dimethyl-4-methoxyphenyl)-2-(4-hydroxyphenyl) ethane.

3,5-dimethyl-4-methoxybenzylbromide is allowed to react first with triethylphosphite and then with p-benzyloxybenzaldehyde according to Canad. J. of Chem. 48 (1970) 1555, to give the substituted stilbene, which after hydrogenation (Pd/C) gives the desired phenol.

4-(3-(2,4,6-trimethoxyphenyl)propyl)phenyl dihydrogen phosphate

EXAMPLE 22

The PG-inhibitory effect of esters of the present invention on the gerbil colon are determined using the general technique described by Eakins, Miller & Karim (J. Pharm. Exp. Ther. 176:441, 1971). Gerbils (Meriones unguiculatus) of own breed, both sexes, weighing 50-80 g are used. The animal is stunned, colon ascendens immediately removed, and a 2–3 cm piece mounted in a 6 ml bath containing a modified de Jalon solution at 28° C and continuously oxygenated. Contractions of the organ are registered either isotonically or isometrically. When testing the inhibitory effect of a compound this is added to the bath 2 min. before the addition of prostaglandin. The antagonist (esters of this invention) is usually dissolved in saline, but occasionally an organic solvent such as ethanol has to be included. Several concentrations of each antagonist are used. In this system prostaglandins $E_1$, $E_2$, $F_{1\alpha}$ and $F_{2\alpha}$ produce suitable contractions of the organ in the concentration range 1–50 ng/ml.

Results from these experiments give an approximation of the PG-inhibitory potency of the compounds. When more precise information about this is desired we use a more elaborate method involving the establishment of several PR dose-response curves in the presence of various concentrations of inhibitor. The method used is essentially the same as that described by Arunlakshana & Schild (Br. J. Pharm. 14:48, 1959). Other agonists, acetylcholine, 5-HT and bradykinin, are included in these experiments in order to determine the selectivity of the antagonism.

Esters of the present invention cause a dose-dependent inhibition of the responses of the gut preparation to either of the prostaglandins tested. The concentration of polyphloretin phosphate (PPP) required to produce a 50 percent reduction of the PG-induced contraction is 10–75 µg/ml, the antagonist-agonist ratio sodium diethylstilbestrol phenyl phosphate is only about one tenth of that of PPP.

The sodium salt of diphenyl phosphate is without effect in concentrations 10 times as high as that of PPP.

In addition the results with other agonists than prostaglandins show that the antagonism is very selective, far higher concentrations than the prostaglandin-inhibitory ones having no influence on the contractions elicited by acetylcholine, 5-HT or bradykinin.

The selective inhibitory effects of the following compounds are found to be equal to or superior to that of PPP.

sodium 2-chloro-4-biphenylyl phenyl phosphate
sodium 2-nitro-4-biphenyl phenyl phosphate
sodium 2,6-dimethyl-4-(2-(4-methoxyphenyl)ethyl)-phenyl phenyl phosphate
sodium 4-(1-ethylidene-2-(4-hydroxyphenyl)-2-butenyl)phenyl phenyl phosphate
sodium 4-(3-(2,4-dimethoxyphenyl)propyl)phenyl phenyl phosphate
sodium 3,5-dimethoxyphenyl 4-(4-(4-hydroxyphenyl)butyl)phenyl phosphate
sodium 4-(2-cyanophenylmethyl)phenyl 3-trifluoromethylphenyl phosphate
sodium 4-(2-N,N-dimethylcarbamoylphenylmethyl)-phenyl 3-acetamidophenyl phosphate
sodium 4-(1-phenyl-1-methylethyl)phenyl 1-naphthyl phosphate
disodium salt of 4-dihydroxyphosphinyloxyphenyl 4-(1-phenyl-1-methylethyl)phenyl hydrogen phosphate
sodium 4-hydroxyphenyl 4-(1-methyl-1-phenylethyl)phenyl phosphate
sodium 4-(1-phenyl-1-methylethyl)phenyl 4-pivaloyloxyphenyl phosphate
sodium 4-(1-(4-hydroxy-3,5-dimethylphenyl)-1-methylethyl)-2,6-dimethylphenyl phenyl phosphate
sodium 2-dimethylaminomethyl-4-(1-(3-dimethylaminomethyl-4-hydroxy-5-methylphenyl)-1-methylethyl)-6-methylphenyl) 3,5-dimethylphenyl phosphate
sodium 4-(3-hydroxy-3-phenylpropyl)phenyl 3,5-dimethylphenyl phosphate
sodium 4-(2-(4-methoxyphenyl)ethyl)-2,6-dimethylphenyl 4-chlorophenyl phosphate
sodium 4-(1-butyl-1-hydroxy-1-phenylmethyl)phenyl 3,5-dimethylphenyl phosphate
sodium 4-methyl-pentyl 4-(2-(phenyl)ethyl)phenyl phosphate
sodium 4-(2-phenylethyl)phenyl 4-(1-methyl-1-phenyl-ethyl)phenyl phosphate
sodium bis(4-(1-(4-hydroxyphenyl)-1-methylethyl)-phenyl) phosphate
trisodium salt of bis(0'-(dihydroxy-phosphinyloxy)-diethylstilbestrol) hydrogen phosphate
sodium 3,5-dimethylphenyl 4-styrylphenyl phosphate
sodium 3,5-dimethylphenyl 2,6-dimethyl-4-(2-(4-methoxyphenyl) ethyl)phenyl phosphate
sodium 3-(2-(3,5-dimethyl-4-methoxyphenyl)ethyl)-phenyl phenyl phosphate
sodium 2,6-dimethyl-4-(2-(3,5-dimethyl-4-methoxyphenyl)ethyl) phenyl phenyl phosphate
sodium 3,5-dimethylphenyl 4-(2,2-diphenylethenyl)-phenyl phosphate
sodium diethylstilbestrol cyclohexyl phosphate
sodium 4-(1-ethyl-2-(4-acetoxyphenyl)-1-butenyl)-phenyl phenyl phosphate
sodium 4-(2-methoxycarbonylphenylmethyl)phenyl 4-methoxyphenyl phosphate
sodium 4-(2-N,N-dimethylcarbamoylphenylmethyl)-phenyl 3-aminophenyl phosphate
disodium 4-(4-(4-carboxylatomethoxyphenyl)-3-hexen-3-yl)phenyl phenyl phosphate
sodium 4-(4-(4-hydroxyphenyl)-3-hexen-3-yl)phenyl 3,5-dimethylphenyl phosphate
sodium 3-(3-(3,5-dimethyl-4-methoxyphenyl)-propyl)phenyl phenyl phosphate
sodium 4-(1-(4-hydroxyphenyl)-1-methylethyl)phenyl 3,5-dimethylphenyl phosphate
sodium bis(4-(3-(2,4,6-trimethoxyphenyl)propyl)-phenyl) phosphate
sodium 4-(1-phenyl-1-methylethyl)phenyl 2-biphenylyl phosphate
sodium 4-(1-acetoxy-1-phenylmethyl)phenyl 3,5-dimethylphenyl phosphate
sodium 2-biphenyl phenyl phosphate
sodium 2-(phenylmethyl)phenyl 4-fluorophenyl phosphate This example shows that the new compounds have utility as antagonists of various prostaglandins and also have the valuable property to exert these effects with high selectivity.

EXAMPLE 23

The inhibitory effect of esters of the present invention has been investigated on the prostaglandin-stimulated corticosterone production by adrenals from male rats in vitro. The experiments were performed using adult Sprague-Dawley male rats weighing 200–250 g, which were housed 1 per cage under conditions of controlled lighting and temperature. Animal quarters were not entered during the 18 h preceding the experiment. The animals were sacrificed by decapitation at 10 AM under conditions chosen to minimize disturbance of the animals. The adrenals were decapsulated and quartered and 8 adrenal quarters from different animals were distributed to 10 ml Erlenmeyer flasks containing 0.5 ml 0.9 % saline and 2.0 ml Krebs-Ringer bicarbonate buffer, ph 7.4. The weight of the adrenal tissue in each flask was determined. The flasks were gassed with 95 % $O_2$ –5 % $CO_2$ and preincubated at 37° C for 1 hour with continuous shaking. Following preincubation the media were decanted and discarded. One ml of Krebs-Ringer buffer, with or without the additions of prostaglandin $E_2$ ($PGE_2$) sodium diethylstilbestrol phenol phosphate (Leo 1227) (for details see below) was added to the flasks, which were then gassed with 95 % $O_2$ - 5 % $CO_2$ and kept at 37° C for 1 hour with continuous shaking. Following incubation, corticosterone levels were determined on 0.5 ml aliquots of the medium by the sulphuric acid fluorescence method.

In the fist experiment (I) $PGE_2$ in a concentration of 1 μg/ml was added to the incubation medium containing the quartered adrenals. The result is shown in the Table and it can be seen that a highly significant increase in the corticosterone concentration is produced by $PGE_2$.

In the next experiment (II) different amounts of Leo 1227 to the incubation medium. The results reveal that when 0.25 and 1 0 mg of Leo 1227 were added to the incubation bath dose-related inhibition of the $PGE_2$-stimulated corticosterone production was seen.

Table

| Exp. no. | Group no. | Additions to incubation media | No. of observ. | Corticosterone production μg/100 mgx 1 h* | P |
|---|---|---|---|---|---|
| | | Control | 4 | 3.8 ± 0.3 | <0.001 |
| I | | $PGE_2$ - 1 μg/ml | 4 | 7.5 ± 0.7 | |
| | A | Leo 1227 - 250 μg/ml | 4 | 3.6 ± 0.4 | A/B |
| | B | $PGE_2$ - 1 μg/ml | 4 | 8.5 ± 0.7 | <0.001 |
| II | C | $PGE_2$ - 1 μg/ml | | | B/C |
| | | Leo 1227 - 250 μg/ml | 4 | 6.2 ± 0.4 | <0.05 |
| | D | $PGE_2$ - 1 μg/ml | | | B/D |
| | | Leo 1227 - 1 mg/ml | 4 | 3.1 ± 0.2 | <0.001 |

*Mean ± standard error

Prostaglandin inhibiting activity of the same order is also seen when the following compounds are tested:
  sodium bis-dienestrol phosphate
  sodium 4-(4-(4-hydroxyphenyl)-3-hexen-3-yl)phenyl 3,5-dimethylphenyl phosphate
  sodium bis(diethylstilbestrol) phosphate
  sodium 4-(1-ethyldiene-2-(4-hydroxyphenyl)-2-butenyl)phenyl phenyl phosphate This example shows that the new compounds are useful to prevent the corticosteroid production in adrenals caused by prostaglandins.

EXAMPLE 24

The action of esters of the present invention on the prostaglandin-stimulated glycolysis of the prepubertal ovary is investigated. The method has been described in detail by Perklev & Ahren (Life Sciences Part I, 10:1387, 1971). In these experiments ovaries from prepubertal rats are removed and placed in Erlenmeyer flasks containing compounds of this invention dissolved in Krebs bicarbonate buffer. After that the ovaries have been preincubated during 60 min. at 37° C in this medium, they are blotted on filter paper and then washed for 2 min. in plain buffer. The ovaries are then transferred to a new incubation medium containing prostaglandins (PG) dissolved in Krebs bicarbonate buffer and incubated at 37° C for 2 hours with continuous shaking. The ovarian glycolysis is then determined by measuring the concentration of lactic acid in the incubation medium. When polyphloretin phosphate (PPP) is present in the preincubation medium in a concentration of 500 μg/ml, the subsequent ovarian lactic acid production produced by $PGE_1$ is reduced to about 50 % of that obtained with ovaries preincubated in plain buffer.

When sodium diethylstilbestrol phenyl phosphate is investigated in the same experimental system, a 50 % reduction of the lactate production is seen, when only 50–100 μg/ml of the compound is present in the preincubation medium. Thus, this compound is 5–10 times more active as a prostaglandin inhibitor than PPP in the present experimental system.

Prostaglandin-inhibiting activity of the same order is also seen when the following compounds are tested:
  sodium bis-dienestrol phosphate
  sodium 4-(4-(4-hydroxyphenyl)-3-hexen-3-yl)phenyl 3,5-dimethylphenyl phosphate
  sodium bis(diethylstilbestrol) phosphate
  sodium 4-(1-ethylidene-2-(4-hydroxyphenyl)-2-butenyl)phenyl phenyl phosphate This example shows that the new compounds are useful to antagonize the effect of prostaglandins on the ovary, which is of importance for the regulation of the hormone secretion from this organ (Behrman, H. R. et al. Am. J. Physiol. 221 (1971) 189).

EXAMPLE 25

The in vivo action of esters of the present invention on the prostaglandin-stimulated glycolysis of the prepubertal ovary is investigated in the following way:

Prepubertal rats, 24–26 days old, of the Sprague-Dawley strain, are injected intraperitoneally (i.p.) with 1 ml saline containing 500 μg sodium diethylstilbestrol phenyl phosphate.

One hour later the animals are sacrificed by cervical fracture and the ovaries are removed and trimmed free of extraneous tissue. The ovaries are then transferred to an incubation bath containing prostaglandin $E_1$ ($PGE_1$; 0.4 μg/ml) dissolved in Krebs bicarbonate buffer and incubated at 37° C for 2 hours with continuous shaking. The ovarian glycolysis is then determined by measuring the concentration of lactic acid in the incubation medium. The details of the method have been described previously (Perklev, T. & Ahren, K., Life Sciences Part I, 10:1387, 1971). In ovaries of animals treated with the phosphoric acid ester mentioned above, the glycolysis is significantly reduced compared to that measured in ovaries injected with saline. The same solution in ovarian glycolysis is also seen when the following compounds are injected i.p. before the exposure of the ovaries to $PGE_1$ as described above:
  sodium bis-dienestrol phosphate
  sodium 4-(4-(4-hydroxyphenyl)-3-hexen-3-yl)phenyl 3,5-dimethylphenyl phosphate
  sodium 4-(1-ethylidene-2-(4-hydroxyphenyl)-2-butenyl)phenyl phenyl phosphate This example shows that the new compounds exert the same effect as shown in the previous experiment also when they are injected into the animals.

EXAMPLE 26

The antagonism to Slow Reacting Substance (SRS) is determined on the isolated guinea-pig ileum as described by Mathe & Strandberg (Acta physiol. scand. 82:460, 1971). Purified SRS is obtained from cat paws perfused with compound 48/80 (Strandberg & Uvnäs: Acta physiol. scand. 82:358, 1971). Sodium diethylstilbestrol phenyl phosphate was tested in this system in several concentrations.

In concentrations as low as 5 µg/ml, it inhibits contractions produced by SRS, but not by histamine and bradykinin, in a competitive manner, i.e. parallel shift of the dose-response curves and with no change in maximum contraction.

The sodium salt of diphenyl phosphate is found to be without effect.

The following compounds of this invention are also found to inhibit SRS:
  sodium 3,5-dimethylphenyl 4-styrylphenyl phosphate
  sodium 2,6-dimethyl-4-(2-(3,5-dimethyl-4-methoxyphenyl)ethyl) phenyl phenyl phosphate
  sodium 4-(1-phenyl-1-methylethyl)phenyl 2-isopropylphenyl phosphate
  sodium 3-(3-(3,5-dimethyl-4-methoxyphenyl)propyl)phenyl phenyl phosphate
  trisodium salt of bis(O'-(dihydroxy-phosphinyloxy)-diethylstrilbestrol) hydrogen phosphate From this example it is obvious that the new compounds also are useful as antagonists of SRS, a compound chemically related to the prostaglandins and known to be one of the substances which provokes bronchial asthma (for references see Brocklehurst, W. E., Progr. Allergy 6(1962) 539).

EXAMPLE 27

The effects of esters of the present invention on the anaphylactic reaction in guinea-pigs have been investigated using the isolated perfused guinea-pig lung preparation as described by Bhattacharya & Delaunois (Arch. Int. Pharmacodyn. 101:495, 1955). Guinea-pigs weighing about 300 g are sensitized with egg albumin according to Fredholm & Strandberg (1969). After the appropriate sensitization period the lungs are removed and mounted in a moist, thermostated chamber. The trachea and A. pulmonalis are cannulated. The arterial cannula is connected to a perfusion fluid reservoir containing Tyrode solution buffered with 10 % Sörensen phosphate buffer. The tracheal cannula is connected with tubing to a carbogen gas supply delivering a constant amount per time unit. The perfusion pressure is measured in a side arm of the tubing with a "Mercury" transducer connected to an Ultralette UV-recorder. When antigen (egg albumin), 0.1 – 1.0 µg, is injected via the arterial cannula, a bronchoconstriction, indicated by an increase in the perfusion pressure, is elicited. When sodium diethylstilbestrol phenyl phosphate 4–20 µg/ml is incorporated in the Tyrode solution this anaphylactic bronchoconstriction is abolished or markedly reduced. The sodium salt of diphenyl phosphate completely lacked such an effect even when tested in the concentration 100 µg/ml.

Similar effects in a dose of about 5–20 µg/ml are also obtained with the following compounds:
  trisodium salt of bis(O'-(dihydroxy-phosphinyloxy)-diethylstilbestrol) hydrogen phosphate
  sodium bis(4-(1-(4-hydroxyphenyl)-1-methylethyl)-phenyl) phosphate
  sodium 2,6-dimethyl-4-(2-(3,5-dimethyl-4-methoxyphenyl)ethyl) phenyl phenyl phosphate This example shows that the new compounds have utility in preventing an anaphylactic reaction.

EXAMPLE 28

Prepubertal rat ovaries are incubated with luteinizing hormone (LH) essentially according to Perklev and Ahren (Life Sciences Part I 10 (1971) 1387), one modification being the inclusion of theophylline into the Krebs-Ringer medium in order to inhibit the breakdown of cyclic AMP. After incubation, the ovaries are homogenized in trichloroacetic acid and cyclic AMP is determined in this extract after removal of the acid. Cyclic AMP is also determined in the incubation medium.

The method for the assay is modelled after that of Gilman (PROC. NATL. ACAD. SCI. U.S. 67 (1970) 305). The extract or the medium containing cyclic AMP is incubated with a protein kinase (prepared from rabbit skeletal muscle) in the presence of a known amount of tritium labelled cyclic AMP. The amount of labelled cyclic AMP bound to the protein kinase is proportional to the amount unlabelled cyclic AMP to be assayed, and is determined by liquid scintillation counting after isolating the kinasecyclic AMP complex by Millipore filtration.

When incubation of the prepubertal ovaries was carried out in the presence of sodium diethylstilbestrol phenyl phosphate the $ID_{50}$ (concentration of inhibitor resulting in 50 % inhibition of the formation of cyclic AMP in the ovary as well as in the incubation medium) was $1.5 \times 10^{-5}$ M.

The following phosphoric acid esters have also been found to exert an inhibiting activity of the same order, when tested in the same in vitro system:
  sodium 2,6-dimethyl-4-(2-(3,5-dimethyl-4-methoxyphenyl)ethyl)phenyl phenyl phosphate
  sodium 4-(1-phenyl-1-methylethyl)phenyl 2-isopropylphenyl phosphate
  sodium 3-(3-(3,5-dimethyl-4-methoxyphenyl)propyl)phenyl pheyl phosphate
  trisodium salt of bis(O'-dihydroxy-phosphinyloxy)-diethylstilbestrol) hydrogen phosphate
  sodium 4-(2-N,N-dimethylcarbamoylphenylmethyl)-phenyl 3-aminophenyl phosphate From this example it is obvious that the new compounds are useful as inhibitors of the formation of cyclic-AMP and therefore will improve pathological conditions caused by an excessive formation of this compound.

EXAMPLE 29

This example illustrates the smooth muscle stimulatory effect of esters of this invention on the gerbil colon in vivo.

The experiments are performed with mongolian gerbils, anesthetized with pentobarbital, 50 mg/kg. The ascending colon is exposed and carefully stretched between silk thread loops and a strain-gauge transducer.

After a stable base-line has been establised an ester of this invention, sodium diethylstilbestrol phenyl phosphate (Leo 1227) is infused i.v.

In doses from 40 mg/kg this treatment causes the gut to respond with a series of contractions. Sodium diphenyl phosphate causes no effect at all in doses up to 400 mg/kg.

When Leo 1227, in the concentration of 1 mg/ml, is incorporated in the buffer solution superfusing the gut, this reacts with an increase in tone, i.e. a contraction.

Similar effects are also obtained with the following compounds trisodium salt of bis(O'-(dihydroxy-phosphinyloxy)-diethylstilbestrol hydrogen phosphate
 sodium bis(4-(1-(4-hydroxyphenyl)-1-methylethyl)-phenyl) phosphate
 sodium 4-(2-N,N-dimethylcarbamoylphenylmethyl)-phenyl 3-aminophenyl phosphate This example shows the usefulness of the new compounds in stimulation of smooth muscles.

EXAMPLE 30

The effects of esters of the present invention on bronchial smooth muscle have been investigated using an isolated perfused guinea-pig lung preparation according to Thattafcharya & Delaunois (Arch. Int. Pharmacodyn. 101:495, 1955). The lungs from guinea pigs weighing 300–400 g are removed, and the trachea and A. pulmonalis cannulated. The arterial cannula is connected to a perfusion fluid reservoir containing Tyrode solution buffered with 10 % Sorensen phosphate buffer. The tracheal cannula is connected with tubing to a carbogen gas supply delivering a constant amount per time unit. The perfusion pressure is measured in a side arm of the tubing with a "Mercury" transducer connected to an Ultralette UV-recorder. The compounds are injected via the arterial cannula, close to the entrance of A. pulmonalis in the lung. In this type of experiments sodium diethylstilbestrol phenyl phosphate showed a broncho-constricting effect, when administered in a dose of about 0.5 mg and upwards. The sodium salt of diphenyl phosphate completely lacked such an effect even when tested in the dose of 12.8 mg.

Similar effects in a dose of about 0.5 – 2.0 mg are also obtained with the following compounds.
 trisodium salt of bis(O'-dihydroxy-phosphinyloxy)-diethylstilbestrol) hydrogen phosphate
 sodium 4-(4-hydroxy-3,5-dimethylphenyl)-1-methylethyl)-2,6- dimethylphenyl phenyl phosphate
 sodium 2-dimethylaminomethyl-4-(1-(3-dimethylaminomethyl-4- hydroxy-5-methylphenyl)-1-methylethyl)-6-methylphenyl) 3,5-dimethylphenyl phosphate
 sodium bis (4-(1-(4-hydroxyphenyl)-1-methylethyl)-phenyl) phosphate This example shows the usefulness of the new compounds in stimulation of smooth muscles.

EXAMPLE 31

Effects of esters of the present invention are also studied on a rat uterus preparation, using an established technique (Staff of the Department of Pharmacology, University of Edinburgh: Pharmacological Experiments on Isolated Preparations, E & S Livingstone Ltd, Edinburgh and London 1968). In these experiments uterine horns from diethylstilbestrol-treated rats are suspended in a 6 ml bath containing modified de Jalon solution, kept at 28° C and gassed with air. When sodium 4-(4-(4-hydroxyphenyl)-3-hexen-3-yl)phenyl 3,5-dimethylphenyl phosphate is added in the concentration range 2–10 μg/ml a contraction is obtained demonstrating the smooth muscle stimulating action of this compound.

Similar effects are also obtained with the following compounds:
 trisodium salt of bis(O'-(dihydroxy-phosphinyloxy)-diethylstilbestrol) hydrogen phosphate
 sodium 2,6-dimethyl-4-(2-(3,5-dimethyl-4-methoxyphenyl)ethyl)- phenyl phenyl phosphate
 disodium 4-(4-(4-carboxylatomethoxyphenyl)-3-hexen-3-yl)phenyl phenyl phosphate This example shows the usefulness of the new compounds in stimulation of smooth muscles.

EXAMPLE 32

| Manufacturing Process for tablets a 25 mg. | | |
|---|---|---|
| Model batch of 1000 tablets. | | |
| I { Sodium bis(4-(3-(2,4,6-trimethoxyphenyl)propyl)phenyl) phosphate mesh 70 | 25.0 | g |
| Lactosum, Ph.Nord. | 210 | g |
| Amylum maidis, Ph.Nord. | 75 | g |
| II { Kollidon 25, B.A.S.F. | 3.5 | g |
| Aqua purificata q.s. | | |
| III { Talcum, Ph.Nord. | 15 | g |
| Magnesii stearas, Ph.Nord. | 1.5 | g |
| Weight of 1000 tablets: | 330 | g |
| Weight of 1 tablet: 330 mg | | |
| Punch: 10.5 mm round, flat, scored, bevel-edged. | | |

Mix the screened substances I thoroughly and then moisten with II, whereupon it is granulated through a stainless sieve no. 10 (mesh 25). Dry the granulate in an oven at a maximum temperature of 40° C, then repeat sieving through sieve no. 10. Add the substances under III and mix thoroughly. Punch tablets with a gross weight of about 330 mg.

EXAMPLE 33

| Manufacturing Process for tablets a 25 mg. | | |
|---|---|---|
| Model batch of 1000 tablets. | | |
| I { Sodium 4-(1-(4-hydroxyphenyl)-1-methylethyl)phenyl 3,5-dimethylphenyl phosphate mesh 70 | 25.0 | g |
| Avicel, FMC Corporation, USA | 76 | g |
| II { Amylum maidis, Ph.Nord. | 76 | g |
| Calcii phosphas, Ph.Nord. | 76 | g |
| III { Talcum, Ph.Nord. | 15 | g |
| Magnesii stearas, Ph.Nord. | 2 | g |
| Weight of 1000 tablets | 270 | g |
| Weight of 1 tablet: 270 mg | | |
| Punch: 9.0 mm round, normal concave. | | |

Mix I by gradual stages with II. Add the substances under III and mix thoroughly. Punch tablets with a gross weight of about 270 mg.

EXAMPLE 34

| Oral suspension 5 mg/ml. | |
|---|---|
| Sodium bis(4-(3-(2,4,6-trimethoxyphenyl)propyl)phenyl)phosphate | 5 mg |
| Sorbitol | 600 mg |
| Ascorbic acid | 100 mg |
| Flavouring compound | q.s. |
| Colour | q.s. |
| Water to make | 1 ml |

EXAMPLE 35

| Vagitoria 25 mg. | |
|---|---|
| Sodium bis(4-(1-(4-hydroxyphenyl-1-methylethyl)phenyl) phosphate | 25 mg |
| Cacao butter | q.s. |

EXAMPLE 36

| Ointment 2 % | | |
|---|---|---|
| Sodium 3,5-dimethylphenyl 2,6-dimethyl-4-(2-(-4-methoxyphenyl)-ethyl)phenyl phosphate | 2 | g |
| Triethanolamine | 1 | g |
| Glycerol | 7 | g |
| Cetanol | 2.5 | g |
| Lanoline | 2.5 | g |
| Stearic acid | 20 | g |
| Sorbitan monooleate | 0.5 | g |
| Sodium hydroxide | 0.2 | g |
| Methyl paraben | 0.3 | g |
| Propyl paraben | 0.1 | g |
| Ethanol | 0.9 | g |
| Water to make | 100 | g |

EXAMPLE 37

| Eye-drops 2 % | |
|---|---|
| Sodium 4-hydroxyphenyl 4-(1-methyl-1-phenylethyl)phenyl phosphate | 20 mg |
| Boric acid | 10 mg |
| Cetylpyridinium chloride | 25 µg |
| Distilled water to make | 1 ml |

EXAMPLE 38

| Aerosol for inhalation | |
|---|---|
| Sodium 4-(2-(4-methoxyphenyl)ethyl)-2,6-dimethylphenyl 4-chlorophenyl phosphate | 1 % |
| Isopropyl myristate | 1 % |
| Dichlorodifluoromethane | 39 % |
| Dichlorotetrafluoroethane | 59 % |

Filled in a container with metered valve. Each dose gives

EXAMPLE 39

| Suspension for injection 20 mg/ml. | |
|---|---|
| Sodium bis(4-(3-(2,4,6-trimethoxyphenyl)propyl)phenyl) phosphate | 20 mg |
| Sodium chloride | 8 mg |
| Carboxy methylcellulose | 1 mg |
| Benzyl alcohol | 1 mg |
| Distilled water to make | 1 ml |

EXAMPLE 40

| Injectable solution 20 mg/ml. | |
|---|---|
| Sodium 4-hydroxyphenyl 4-(1-methyl-1-phenylethyl)phenyl phosphate | 20 mg |
| Ascorbic acid | 1 mg |
| Sodium bisulfite | 1 mg |
| Sodium chloride | 6 mg |
| Methyl paraben | 0.7 mg |
| Propyl paraben | 0.3 mg |
| Distilled water to make | 1 ml |

EXAMPLE 41

| Injectable solution 25 mg/ml. | |
|---|---|
| Sodium 4-methyl-pentyl 4-(2-(phenyl)-ethyl)phenyl phosphate | 25 mg |
| Benzyl alcohol | 50 mg |
| Peanut oil to make | 1 ml |

EXAMPLE 42

| 40 mg Sterile powder to be dissolved in water for injection. | |
|---|---|
| Sodium 4-hydroxyphenyl 4-(1-methyl-1-phenylethyl)phenyl phosphate | 40 mg |
| Sodium chloride | 4 mg |
| Methyl paraben | 0.7 mg |
| Propyl paraben | 0.3 mg |

The substances are dissolved in distilled water.

The solution is dispensed in vials and freeze-dried.

The above examples 32 – 42 to compositions are merely representative with regard to the active ingredients exemplified. It is to be understood that other compounds disclosed in the foregoing examples 1 – 18 may well be substituted for the active ingredients illustrated in the above examples. Also, it is to be noted that two or more compounds of the invention may be used in combination in the compositions illustrated, and also, if desired, in combination with other pharmacologically active agents.

Various modifications and equivalents will be apparent to one skilled in the art and may be made in the compounds, compositions and methods of the present invention without departing from the spirit or scope thereof, and it is therefore to be understood that the invention is not to be limited to the specific examples and embodiments disclosed herein.

We claim:

1. A novel secondary phosphoric acid ester compound having the general formula $$A-O-\overset{\overset{O}{\|}}{\underset{\underset{OM}{|}}{P}}-O-B \qquad (I)$$

wherein M is selected from the group consisting of hydrogen and a pharmaceutically acceptable inorganic and organic cation, and wherein A and B, independent of each other, are wherein one and only one of the substituents R⁶, R⁷, and R¹³ always represents a group R, located in any of the ortho, meta and para positions relative to the phosphoric acid ester group, the group R having the formula

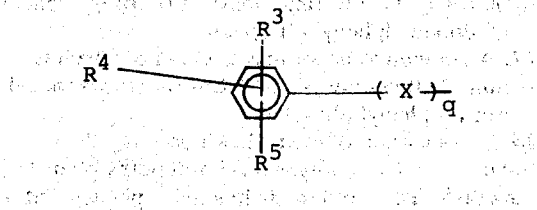

wherein q is selected from the group consisting of zero and one, and wherein X is selected from the group consisting of: straight saturated hydrocarbon chains having at most 4 carbon atoms; and straight hydrocarbon chains having 2 to 4 carbon atoms and containing one double bond; wherein X above may be substituted by at most two substituents selected from the group consisting of: lower alkyl; lower alkenyl; cyclopentyl; cyclohexyl; phenyl; phenyl substituted in m- or p- position by one substituent selected from the group consisting of lower alkyl, lower alkoxy, —F, Cl, —Br, and —CF₃; benzyl; benzyl substituted in m- or p- position by one substituent selected from the group consisting of lower alkyl, lower alkoxy, —F, —Cl, —Br, and —CF₃; benzylidene; benzylidene substituted in m- or p- position by one substituent selected from the group consisting of lower alkyl, lower alkoxy, —F, —Cl, —Br, and —CF₃; and lower alkylidene; with the proviso that not more than one substituent selected from the group consisting of: cyclopentyl; cyclohexyl; phenyl; substituted phenyl; benzyl; substituted benzyl; benzylidene; and substituted benzylidene is present in X; wherein B in the general formula (I) above also may be selected from the group consisting of: alkyl, having one to eight carbon atoms, inclusive, being at most di-substituted; cycloalkyl, namely cyclopentyl and cyclohexyl, being at most di-substituted; 1- and 2-naphthyl, both naphthyls being at most di-substituted; and

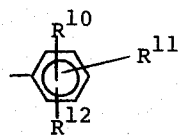

wherein the substituents in B, when B is alkyl, having one to eight carbon atoms, inclusive; cycloalkyl; or naphthyl, are selected from the group consisting of lower alkyl, lower alkoxy, —F, —Cl, —Br, and —CF₃; wherein R³, R⁴, R⁵, R⁶, R⁷, R¹⁰, R¹¹, R¹², and R¹³ above are selected from the group consisting of: hydrogen; lower alkyl; lower alkenyl; lower alkoxy; hydroxy; —O—CO—R¹⁴; —F; —Cl; —Br; —CF₃; where R¹⁴ is lower alkyl; with the proviso that always one of the substituents, being attached to an aromatic group of A or B as defined above, is selected from the group consisting of lower alkoxy; hydroxy; and —O—CO—R¹⁴.

2. A compound according to claim 1, wherein at least one of the substituents R¹⁰, R¹¹, and R¹² is hydrogen; and wherein at least one of the substituents R³, R⁴, R⁵, R⁶, R⁷, R¹⁰, R¹¹, R¹², and R¹³, in addition to one being R, is different from hydrogen; R having the meaning given in claim 1.

3. A compound according to claim 2, wherein the substituent R, having the meaning given in claim 1, is located in one of the m- and p-positions relative to the secondary phosphoric acid ester group.

4. A compound according to claim 3, wherein q is one and wherein X is selected from the group consisting of straight hydrocarbon chains having at most three carbon atoms; and straight hydrocarbon chains having at most three carbon atoms and being substituted with at most two substituents selected from the group consisting of lower alkyl, lower alkenyl, and lower alkylidene.

5. A compound according to claim 3, wherein q is one; wherein X is a straight hydrocarbon chain having at most three carbon atoms and being substituted with a substituent selected from the group consisting of phenyl, substituted phenyl, benzyl, substituted benzyl, benzylidene, and substituted benzylidene; and wherein B is selected from the group consisting of alkyl, having one to eight carbon atoms, inclusive and being at most disubstituted, and

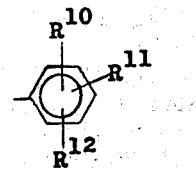

wherein R¹⁰, R¹¹, and R¹² have the meaning given in claim 1.

6. A compound according to claim 4, wherein B is equal to A; A having the meaning given in claim 1.

7. A compound according to claim 4, wherein B is

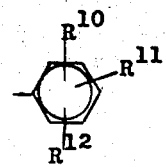

wherein R¹⁰, R¹¹, and R¹² have the meaning given in claim 1.

8. A compound according to claim 4, wherein B is an alkyl group having at least four carbon atoms, and being at most di-substituted.

9. A compound according to claim 6, wherein at least two of the substituents R³, R⁴, R⁵, R⁶, R⁷, and R¹³, except the one being R, are selected from the group consisting of lower alkyl, lower alkoxy, hydroxy, and —O—CO—R¹⁴; the remaining ones being hydrogen; R and R¹⁴ having the meaning given in claim 1.

10. A compound according to claim 7, wherein at least two of the substituents R³, R⁴, R⁵, R⁶, R⁷, and R¹³, except the one being R, are selected from the group consisting of lower alkyl, lower alkoxy, hydroxy, and —O—CO—R¹⁴; the remaining ones being hydrogen; R and R¹⁴ having the meaning given in claim 1.

11. A compound according to claim 1, wherein M is selected from the group consisting of calcium, potassium, sodium diethanolamine, dimethylaminoethanol and N-methylglucamine.

12. A compound according to claim 5, selected from the group consisting of sodium 4-(2,2-bis(4-methoxyphenyl)ethenyl)phenyl 3,5-dimethylphenyl phosphate sodium 4-(1-(4-hydroxyphenyl)-2-(4-fluorophenyl)ethyl)phenyl 3,5-dimethylphenyl phosphate 13. A compound according to claim 6, selected from the group consisting of
   sodium bis(4-(1-(4-hydroxyphenyl)-1-methylethyl)phenyl) phosphate
   sodium bis(diethylstilbestrol) phosphate
   sodium bis(4-(2-(4-butoxyphenyl)-1-ethyl-1-butenyl)phenyl) phosphate
   sodium bis(dienestrol) phosphate
   sodium bis(2-allyl-4-(1-(3-allyl-4-hydroxyphenyl)-1-methylethyl)phenyl) phosphate and
   sodium bis(2-fluoro-4-(1-(3-fluoro-4-hydroxyphenyl)-1-methylethyl)phenyl) phosphate.

14. A compound according to claim 9, selected from the group consisting of
   sodium bis(4-(2-(4-methoxyphenyl)-ethyl)-2,6-dimethylphenyl) phosphate
   sodium bis(4-(2-(4-methoxy-3,5-dimethylphenyl)ethyl)phenyl) phosphate
   sodium bis(4-(3-(2,4-dimethoxyphenyl)propyl)phenyl)phosphate
   sodium bis(4-(3-(2,4,6-trimethoxyphenyl)propyl)phenyl) phosphate 15. A compound according to claim 7, selected from the group consisting of
   sodium diethylstilbestrol phenyl phosphate
   sodium 4-(1-ethylidene-2-(4-hydroxyphenyl)-2-butenyl)phenyl phenyl phosphate 16. A compound according to claim 10, selected from the group consisting of
   sodium 2,6-dimethyl-4-(2-(4-methoxyphenyl)ethyl)phenyl phenyl phosphate
   sodium 4-(2-(4-methoxyphenyl)ethyl)-2,6-dimethylphenyl 4-chlorophenyl phosphate
   sodium 3,5-dimethylphenyl 2,6-dimethyl-4-(2-(4-methoxyphenyl)ethyl)phenyl phosphate
   sodium 3-(2-(3,5-dimethyl-4-methoxyphenyl)ethyl)phenyl phenyl phosphate
   sodium 2,6-dimethyl-4-(2-(3,5-dimethyl-4-methoxyphenyl)ethyl) phenyl phenyl phosphate
   sodium 4-(3-(2,4-dimethoxyphenyl)propyl)phenyl phenyl phosphate
   sodium 3-(3-(3,5-dimethyl-4-methoxyphenyl)propyl)phenyl phenyl phosphate
   sodium 4-(3-(2,4,6-trimethoxyphenyl)propyl)phenyl 3,5-dimethylphenyl phosphate 17. A compound according to claim 8, which is
   sodium 2-ethyl-butyl 4-(3-(2,4,6-trimethoxyphenyl)propyl) phenyl phosphate 18. A compound of claim 1, which is
   sodium 4-(1-(4-hydroxy-3,5-dimethylphenyl)-1-methylethyl)-2,6-dimethylphenyl phenyl phosphate.

19. A compound of claim 1, which is selected from the group consisting of:
   sodium 4-(1-(4-acetoxy-3,5-dimethylphenyl)-1-methylethyl)-2,6-dimethylphenyl phenyl phosphate,
   sodium ethyl 4-(2-(4-methoxy-3,5-dimethylphenyl)ethyl)-2,6-dimethylphenyl phosphate,
   sodium diethylstilbestrol cyclohexyl phosphate,
   sodium 4-(1-ethyl-2-(4-acetoxyphenyl)-1-butenyl)phenyl phenyl phosphate,
   sodium 4-(1-(4-hydroxyphenyl)-2-(trifluoromethylphenyl)ethyl) phenyl 3,5-dimethylphenyl phosphate,
   sodium 4-(1-(4-hydroxyphenyl)-2-(3-methylphenyl)ethyl)phenyl 3,5-dimethylphenyl phosphate, and
   sodium 4-(1-(4-hydroxyphenyl)-2-(4-fluorophenyl)ethenyl)phenyl 3,5-dimethylphenyl phosphate.

20. A composition of matter comprising as an active ingredient a compound according to claim 1 in combination with a pharmaceutically acceptable carrier.

21. A method of treating a living animal body suffering from the actions of an excessive formation and release of endogenous prostaglandin or exposure to exogenous prostaglandin, comprising administration of a therapeutically-effective amount of a compound of claim 1 to said animal body.

* * * * *

UNITED STATES PATENT OFFICE
CERTIFICATE OF CORRECTION

Patent No. 3,989,825          Dated Nov. 2, 1976

Inventor(s) Bertil Hogberg, Hans Fex, Torsten Perklev, Sten Veige & Bogoran Fredholm It is certified that error appears in the above-identified patent and that said Letters Patent are hereby corrected as shown below:

In the heading of [75], Line 3, Change "Bogoran Fredholm", to read --- Bo Goran Fredholm---

Col. 7, Line 18; Change "-CN;-CN;-$NO_2$" to read --- -CN; -$NO_2$---

Col. 9, Line 57; Change "ether group" to read ---ester group---

Col. 19, Line 3; Change "bis(4-1-(4-hydroxy" to read ---bis(4-(1-(4-hydroxy ---

Col. 19, Line 16; Change "bis(2-ethyl-3-2-(2-ethyl" to read ---bis(2-ethyl-3-(2-(2-ethyl---

Col. 20, Line 67; Change "trichloroacetamido" to read ---trichloroacetamide---

Col. 23, Line 11; Change "dichloro-4biphenylyl" to read ---dichloro-4-biphenylyl---

Col. 28, Line 6; Change "2-nitro-2-biphenylyl" to read ---2-nitro-4-biphenylyl---

Col. 29, Line 49; Change "2,2bis(4-" to read --- 2,2-bis(4- ---

Col. 33, Line 12; Change "fist" to read ---first---

Col. 37, Line 44; Change "sodium 4-(4-hydroxy" to read ---Sodium 4-(1-(4-hydroxy---

UNITED STATES PATENT OFFICE
CERTIFICATE OF CORRECTION

Patent No. 3,989,825       Dated Nov. 2, 1976

Inventor(s) Bertil Hogberg, Hans Fex, Torsten Perklev, Sten Veige and Bogoran Fredholm It is certified that error appears in the above-identified patent and that said Letters Patent are hereby corrected as shown below:

CLAIM 1 Col. 41, Line 26; Change "-F,Cl,-Br," to read --- -F,-Cl, -Br, ---

Signed and Sealed this

Twenty-ninth Day of November 1977

[SEAL]

Attest:

RUTH C. MASON  
Attesting Officer

LUTRELLE F. PARKER  
Acting Commissioner of Patents and Trademarks

UNITED STATES PATENT OFFICE
CERTIFICATE OF CORRECTION

Patent No. 3,989,825          Dated Nov. 2, 1976

Inventor(s) Knut Bertil Högberg et al.

It is certified that error appears in the above-identified patent and that said Letters Patent are hereby corrected as shown below:

Col. 31, line 24 has an omission after "antagonist-agonist ratio"; should read --- antagonist-agonist ratio being in the order of 2000-4000. The corresponding concentration of ---

Claim 15, Col. 43, line 27, the last five lines of the claim have been dropped; should read --- sodium 4-hydroxyphenyl 4-(1-methyl-1-phenylethyl)phenyl phosphate ---
--- sodium 4-(1-phenyl-1-methylethyl) phenyl 4-pivaloyloxyphenyl phosphate ---
---sodium 4-(1-(4-hydroxyphenyl)-1-methylethyl)phenyl 3,5-dimethylphenyl phosphate ---

Signed and Sealed this

Thirty-first Day of January 1978

[SEAL]

Attest:

RUTH C. MASON          LUTRELLE F. PARKER
Attesting Officer        Acting Commissioner of Patents and Trademarks